(12) United States Patent
Puerta et al.

(10) Patent No.: US 8,242,309 B2
(45) Date of Patent: Aug. 14, 2012

(54) CATIONIC ALCOHOLS AND USES THEREOF

(75) Inventors: David T. Puerta, Melrose, MA (US); Lorna Nagamoottoo-Casse, Boston, MA (US); Kevin T. Love, Boston, MA (US)

(73) Assignee: Living Proof, Inc., Cambridge, MA (US)

( * ) Notice: Subject to any disclaimer, the term of this patent is extended or adjusted under 35 U.S.C. 154(b) by 91 days.

(21) Appl. No.: 12/883,762

(22) Filed: Sep. 16, 2010

(65) Prior Publication Data

US 2011/0070179 A1    Mar. 24, 2011

Related U.S. Application Data

(60) Provisional application No. 61/243,066, filed on Sep. 16, 2009, provisional application No. 61/320,362, filed on Apr. 2, 2010.

(51) Int. Cl.
*C07C 213/00* (2006.01)
*C11D 1/62* (2006.01)

(52) U.S. Cl. .................... 564/281; 424/70.28

(58) Field of Classification Search ........... 564/281
See application file for complete search history.

(56) References Cited

U.S. PATENT DOCUMENTS

| | | | |
|---|---|---|---|
| 3,883,596 A | 5/1975 | Hager et al. | 260/609 R |
| 3,972,855 A | 8/1976 | Martinsson et al. | 260/567.6 M |
| 4,000,175 A | 12/1976 | Foulletier et al. | 260/459 R |
| 4,165,338 A | 8/1979 | Katsushima et al. | 260/584 R |
| 4,183,367 A | 1/1980 | Goebel et al. | 132/7 |
| 4,377,710 A | 3/1983 | Seale et al. | 564/281 |
| 4,420,434 A | 12/1983 | Falk | 260/501.12 |
| 4,577,036 A | 3/1986 | Falk | 549/556 |
| 4,638,089 A | 1/1987 | Hisamoto et al. | 564/292 |
| 4,778,675 A | 10/1988 | Vanlerberghe et al. | 424/70 |
| 4,836,958 A | 6/1989 | Karydas | 260/501.15 |
| 4,841,090 A | 6/1989 | Patel | 558/437 |
| 5,132,425 A | 7/1992 | Sotoya et al. | 544/401 |
| 5,160,733 A | 11/1992 | Berthiaume et al. | 424/71 |
| 5,679,330 A | 10/1997 | Matsuo et al. | 424/70.19 |
| 5,696,291 A | 12/1997 | Bechara et al. | 564/292 |
| 6,444,213 B1 | 9/2002 | Morita et al. | 424/401 |
| 6,608,230 B2 | 8/2003 | Klaas et al. | 568/589 |
| 7,164,041 B1 | 1/2007 | Moore et al. | 564/82 |
| 7,534,274 B2 | 5/2009 | Lee | 44/434 |

FOREIGN PATENT DOCUMENTS

| | | |
|---|---|---|
| EP | 0 477 057 A1 | 3/1992 |
| GB | 1 268 636 | 3/1972 |
| GB | 1 312 675 | 4/1973 |
| GB | 1 598 567 | 9/1981 |
| JP | 63-154608 | 6/1988 |
| JP | 2001-122893 | 5/2001 |
| JP | 2001-1199845 | 7/2001 |
| WO | 99/26594 | 6/1999 |
| WO | 2008/012747 | 1/2008 |

OTHER PUBLICATIONS

Conte et al, Regioselective Ring Opening of [(perfluoroalkyl)methyl] Oxiranes with N-nucleophiles, J. Fluorine Chem., vol. 126, Issues 9-10, pp. 1274-1280 (2005).*
International Search Report from International Application No. PCT/US10/49134 dated Oct. 26, 2010.

* cited by examiner

*Primary Examiner* — Patricia A Duffy
*Assistant Examiner* — Dennis J Parad
(74) *Attorney, Agent, or Firm* — Fitzpatrick, Cella, Harper & Scinto

(57) ABSTRACT

Compositions are disclosed comprising novel fluorinated cationic alcohols in a cosmetically acceptable vehicle. The fluorinated compounds alter a surface property of the hair to provide hair conditioning, for example. In embodiments, the compounds have improved water solubility and deposition properties.

25 Claims, 4 Drawing Sheets

Feel Test: Shampoo and Conditioner Level 1 Damaged Hair

Feel Test: Total Scores on Level 1 Damaged Hair

Feel Test: Shampoo and Conditioner Level 2 Damaged Hair

Feel Test: Total Scores on Level 2 Damaged Hair

Feel Test: Shampoo and Conditioner Level 3 Damaged Hair

Feel Test: Total Scores on Level 3 Damaged Hair

Feel Test: Plot of Averaged Total Feel Scores Normalized per Assessor

CATIONIC ALCOHOLS AND USES THEREOF

This application claims the benefit of U.S. Provisional Application No. 61/243,066, filed on Sep. 16, 2009 and U.S. Provisional Application No. 61/320,362, filed Apr. 2, 2010, all of which are incorporated herein by reference.

BACKGROUND OF THE INVENTION

1. Field of the Invention

The invention is directed to cationic fluorinated alcohols, compositions containing the same, and methods for treating surfaces such as hair and skin.

2. Description of Related Art

Hair conditioning refers to the process of imparting attributes such as smoothness, softness, and ease of styling to hair. Conditioning may also reduce a feeling of dryness and impart shine. Both damaged and normal hair require conditioning, however, there is a greater need of conditioning for damaged hair due to the negative attributes it imparts. There is no single sensory attribute that equates with the perception of damage, rather it is associated with a combination of tactile and visual properties. For example, damaged hair in general is more hydrophilic leaving it susceptible to moisture flux which increases its propensity for swelling and breakage leading to a rough texture. Additionally, damaged hair tends to have a duller appearance due to the scattering of light from its rough, non-uniform surface. Hair damage may be caused by environmental factors, such as chemical attack from bleaches, dyes and pollutants, photodamage from the sun, heat damage from a dryer or flat iron, or mechanical damage from styling. However, a perception of damage may also arise when hair has not been subject to these environmental factors, but from the hair being coarse or varied in lipid content and specific lipid composition. Improving upon benefits such as hydrophobicity, shine and tactile properties leads to the perception of healthier, more conditioned hair.

Among the best known hair conditioners are long chain quaternary ammonium compounds and fatty alcohols which have been used extensively in the prior art. The positively charged ammonium moiety of long chain quaternary ammonium compounds is attracted to the negatively charged surfaces of the keratin fibers, while the long chain portions of these molecules form a coating on the hair to create a perception of smoothness and increase the manageability of the hair.

Silicones are also widely used in hair conditioner products. These products likewise form a coating on the hair shaft, and may be provided with an amino functionality or other chemical functionality to impart charge. Silicones are frequently copolymerized and co-formulated with other polymers to provide a product having a combination of attributes.

The principle sensory drawback associated with all of the prior art conditioners is that the hair tends to feel coated and heavy, driving the consumer to wash and re-style their hair more frequently, leading to further damage. In addition to silicones, the oleophilic portions of fatty alcohols and higher molecular weight quatenary compounds may cause hair to feel oily. Additionally, the majority of compounds used to provide shine properties to hair are typically oils and silicones, leading to a somewhat undesirable tactile perception over time.

Thus, there is an unmet need in the art for robust conditioning compositions that can be used to condition hair that is perceived as being damaged, without the sensory drawbacks associated with the prior art compositions.

Cationic molecules have been used extensively for various applications including hair and skin conditioning, surface modification, as wetting agents, and industrial surfactants. Fluorinated compounds have also been used in cosmetic formulations. For example, GB Application No. 1 598 567 discloses fluorinated surfactants such as Zonyl® used in combination with silicones in a hair conditioner in an effort to render the conditioner more grease resistant, i.e., less oily.

U.S. Pat. Nos. 7,763,240 and 7,785,575 (which are assigned to the assignee herein) describe fluorinated compounds useful in hair care products to control moisture penetration into the hair (frizz control). Compositions containing these compounds resist dirt, avoid a feeling of greasiness or oiliness in the hair and leave a low amount of residue (i.e., are "weightless").

It has now been discovered that certain cationic fluorinated alcohols, which can be synthesized by the reaction of a fluorinated epoxide and a tertiary amine, have novel and beneficial effects when applied to hair. These compounds have improved deposition properties, so that they impart an improved feel to damaged, dry and coarse hair, without the sensory drawbacks associated with the prior art. More specifically, certain inventive compounds described herein have demonstrated significant deposit from rinse out formulations, leading to positive attributes such as increasing the contact angle of damaged hair, imparting shine which lasts through shampoo cycles, and reducing friction on damaged ends.

In embodiments, the compounds and compositions described herein are capable of modifying or treating surfaces including skin, hair, fabrics, solids, and may be employed as surfactants and/or surface modifying agents for improving chemical reactions.

SUMMARY OF THE INVENTION

In one aspect, the invention is a class of novel fluorinated cationic alcohols according to the following formula (I), including cosmetically acceptable salts thereof:

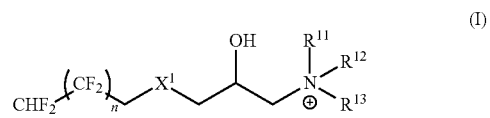

wherein, $X^1$ is O or —$(CH_2)_m$— (m being an integer between 1 and 20); $R^{11}$, $R^{12}$ and $R^{13}$ are independently $C_{1-6}$ alkyl or $C_{1-6}$ hydroxyalkyl; and n is an integer from 1 to 20. These compounds are non-perfluorinated, preferably having a terminal $CHF_2$ group, and thus may be readily distinguished from the perfluorinated surfactants used in the prior art for a variety of purposes.

Alternatively, $X^1$ is the residue of a hydroxy-reactive linker used in the synthesis, such as a poly glycol (e.g., polypropylene glycol (PPG) or polyethylene glycol (PEG)). In the case of PEG used as a starting material, $X^1$ is —$(CH_2—CH_2—O)_p$— (wherein p is an integer from 1 to 10,000, depending on the molecular weight of the PEG starting material). In such embodiment, the definitions of the other groups are the same as in the preceding paragraph.

In embodiments, the compound according to formula (I) has the following structure:

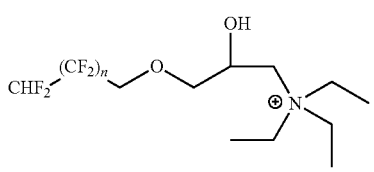

(II)

including cosmetically acceptable salts thereof, wherein n is an integer from 1 to 20.

In another aspect the invention is a compound according to Formula (III) comprising two or more linked quaternary moieties.

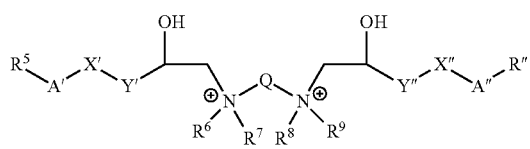

(III)

including cosmetically acceptable salts.

In Formula (III), A' and A" are independently $CH_2$, CHF or $CF_2$; X' and X" are independently O, $CF_2$, or $—(CH_2)_m—$; Y' and Y" are independently $CH_2$, CHF or $CF_2$; $R^5$ and $R^{10}$ are the same or different organic groups, each substituted with at least two fluorine atoms; $R^6$ and $R^9$ are independently substituted or unsubstituted $C_{1-6}$ alkyl, and may join to form a ring; $R^7$ and $R^8$ are independently substituted or unsubstituted $C_{1-6}$ alkyl, and may join to form a ring; n is an integer from 1 to 20; and m is an integer from 1 to 20. Q is a divalent alkyl, alkenyl, alkynyl, alkoxy, cycloalkyl, aryl, alkoxy; acyl; acyloxy; heterocycloalkyl, hydroxyalkyl, thioalkyl; aliphatic; heteroaliphatic; cycloaryl; or heteroaryl group; any of which may be substituted or unsubstituted, linear or branched. For example, Q may be $—(CH_2)_t—$; $—CH_2CH_2O)t—$; $—(CH_2CH(CH_3)—O)t—$; $—(CH_2CH(OH)—CH_2)t—$; $—(CH_2C(=O))t—$; $—(CH_2S—CH2)t—$ (wherein t is an integer from 1 to 10,000).

In embodiments, the compound according to Formula (III) is not perfluorinated. For example, $R^5$ and $R^{10}$ may be identical straight or branched chain $C_{1-30}$ fluoroalkyl groups having a terminal $CHF_2$ group.

In embodiments, the compound according to Formula (III) comprises two identical quaternary moieties linked by an alkylene group, so that A' and A" are the same, X' and X" are the same, Y' and Y" are the same, $R^5$ and $R^{10}$ are the same; $R^6$ is the same as $R^8$; and $R^7$ is the same as $R^9$.

In other embodiments, the compound according to Formula (III), is provided with one or more additional cationic quaternary moieties, so that one or more of $R^6$, $R^7$, $R^8$, and $R^9$ is defined by the following formula:

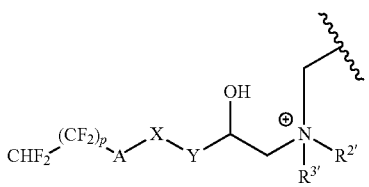

(IV')

wherein, X is O, $CF_2$, or $—(CH_2)_q—$; A is $CH_2$, CFH or $CF_2$; Y is $CH_2$, CFH or $CF_2$; $R^{2'}$ and $R^{3'}$ are independently hydrogen; aliphatic; heteroaliphatic; acyl; aryl; or heteroaryl; any of which may be substituted or unsubstituted; or any of $R^{2'}$, and $R^{3'}$ may join to form a ring with a quaternary nitrogen; p is an integer from 1 to 20; and q is an integer from 1 to 20.

In another aspect, the compound according to Formula (III) takes the form of Formula (III') in which the quaternary moieties are linked by an alkylene group:

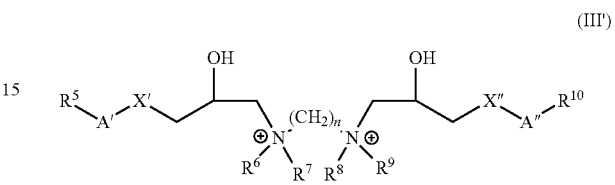

(III')

including cosmetically acceptable salts.

In Formula (III'), A' and A" are independently $CH_2$, CHF or $CF_2$; X' and X" are independently O, $CF_2$, or $—(CH_2)_m—$; $R^5$ and $R^{10}$ are the same or different organic groups, each substituted with at least two fluorine atoms; $R^6$ and $R^9$ are independently substituted or unsubstituted $C_{1-6}$ alkyl, and may join to form a ring; $R^7$ and $R^8$ are independently substituted or unsubstituted $C_{1-6}$ alkyl, and may join to form a ring; n is an integer from 1 to 20; and m is an integer from 1 to 20.

In embodiments, the compound according to Formula (III') is not perfluorinated. For example, $R^5$ and $R^{10}$ may be identical straight or branched chain $C_{1-30}$ fluoroalkyl groups having a terminal $CHF_2$ group.

In embodiments, the compound according to Formula (III') comprises two identical quaternary moieties linked by an alkylene group, so that A' and A" are the same, X' and X" are the same, $R^5$ and $R^{10}$ are the same; $R^6$ is the same as $R^8$, and $R^7$ is the same as $R^9$.

In other embodiments, the compound according to Formula (III'), is provided with one or more additional cationic quaternary moieties, so that one or more of $R^6$, $R^7$, $R^8$, and $R^9$ is defined by the following formula:

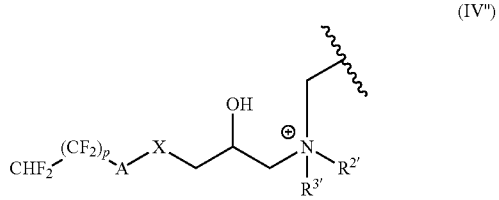

(IV")

wherein, X is O, $CF_2$, or $—(CH_2)_q—$; A is $CH_2$, CFH or $CF_2$; $R^{2'}$ and $R^{3'}$ are independently hydrogen; aliphatic; heteroaliphatic; acyl; aryl; or heteroaryl; any of which may be substituted or unsubstituted; or any of $R^{2'}$, and $R^{3'}$ may join to form a ring with a quaternary nitrogen; p is an integer from 1 to 20; and q is an integer from 1 to 20.

In still another aspect, the invention is a composition for treating skin or hair, comprising a cosmetically acceptable excipient, and a compound of formula (III) or (III'), as described above, or a cosmetically acceptable salt thereof.

In still another aspect, the invention is a method for treating hair comprising applying to hair a composition comprising the compound according to Formula (III) or (III'), in an amount effective to alter a surface property of the hair.

In another aspect, the invention is a composition for treating skin or hair, comprising a cosmetically acceptable excipient and a compound of formula (IV) including cosmetically acceptable salts thereof

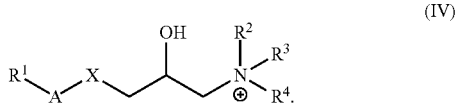

(IV)

In Formula (IV), X is O, $CF_2$, or $—(CH_2)_m—$ (wherein m is 1 to 20); A is $CH_2$, CHF or $CF_2$; $R^1$ is an organic group substituted with at least two fluorine atoms; $R^2$, $R^3$, and $R^4$ are independently aliphatic; heteroaliphatic; alkoxy; acyl; aryl; or heteroaryl; any of which may be substituted or unsubstituted; and any of $R^2$, $R^3$, and $R^4$ may join to form one or more rings. In embodiments, one or more of $R^2$, $R^3$, and $R^4$ contains at least one fluoro substituent. These fluorinated alcohols have not previously been used in a hair conditioning composition. Compositions for treating hair containing perfluorinated compounds according to Formula (IV) are within the scope of the invention, but non-perfluorinated compounds are presently preferred. For example, $R^1$ may be a $C_{1-30}$ straight or branched chain fluoroalkyl group with a terminal $CHF_2$ group.

In an alternative embodiment, X in formula (I) is the residue of a hydroxy-reactive linker used in the synthesis, including without limitation, a poly glycol (e.g., polypropylene glycol (PPG) or polyethylene glycol (PEG)). In the case of PEG used as a starting material, for example, X may be $—(CH_2—CH_2—O)_p—$ (wherein p is an integer from 1 to 10,000, depending on the molecular weight of the PEG starting material). In such embodiment, the definitions of A, $R^1$, $R^2$, $R^3$, and $R^4$ are the same as for the embodiment described in the preceding paragraph.

In another aspect, the invention is a corresponding method of treating hair, comprising applying to hair a composition comprising a compound of formula (IV), as defined above.

In another aspect, the invention is a cosmetic composition for treating hair or skin comprising the reaction product of a fluorinated epoxide and a tertiary amine and a cosmetically acceptable excipient, said reaction product comprising a quaternary ammonium moiety, a hydroxyl group, and containing at least two fluorine atoms. In embodiments the tertiary amine is a diamine. In embodiments the fluorinated epoxide is not perfluorinated.

In still another aspect, the invention is a method of treating hair comprising applying a cosmetic composition comprising the reaction product of a fluorinated epoxide and a tertiary amine.

DETAILED DESCRIPTION OF THE PREFERRED EMBODIMENTS

Definitions

Figure 1:
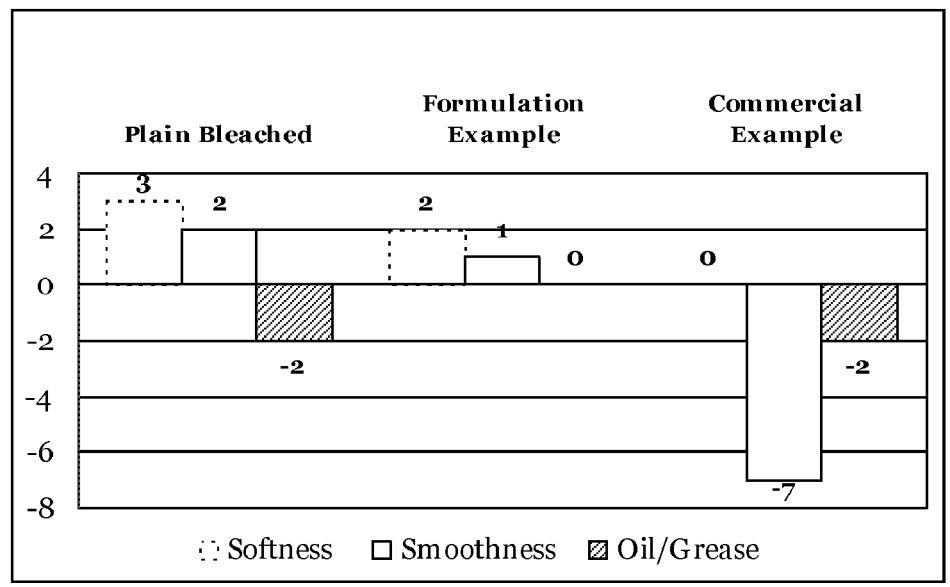
FIG. 1 depicts the results of a feel test comparison in which three principle feel parameters were assessed on hair treated with a shampoo and conditioner (Formulation Examples 2 and 3 respectively) according to the invention, hair treated with a leading prior art conditioning shampoo, and a control.
Figure 2:
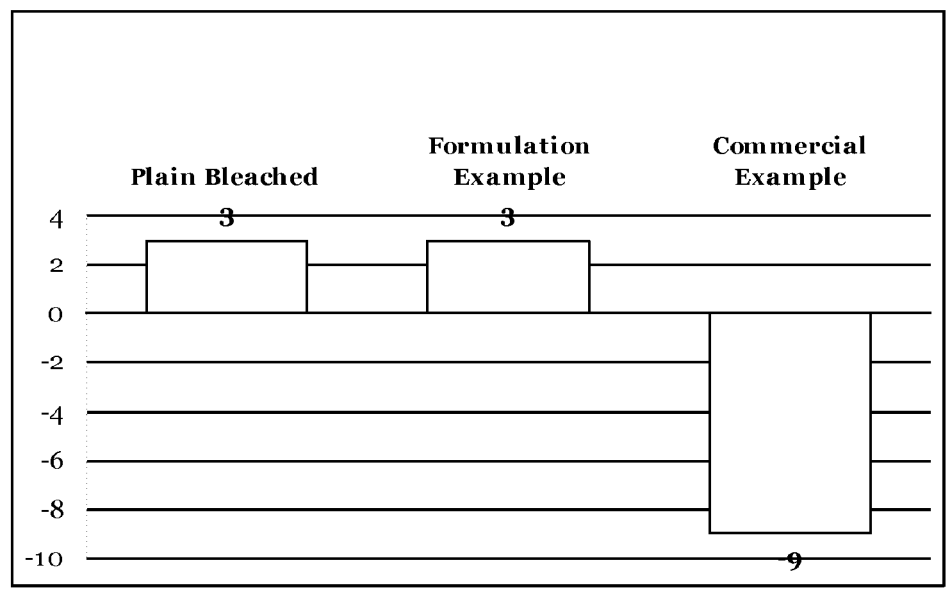
FIG. 2 depicts the results of the comparison of FIG. 1, with the parameters totaled.
Figure 3:
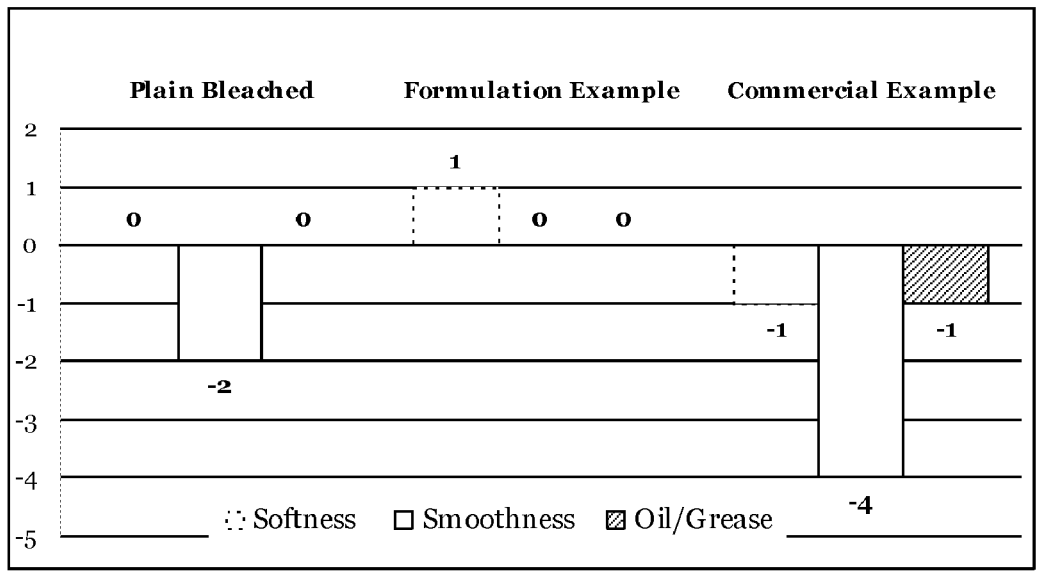
FIG. 3 depicts the results of a feel test comparison, similar to the test conducted in FIG. 1, except that the test is conducted on more severely damaged hair.
Figure 4:
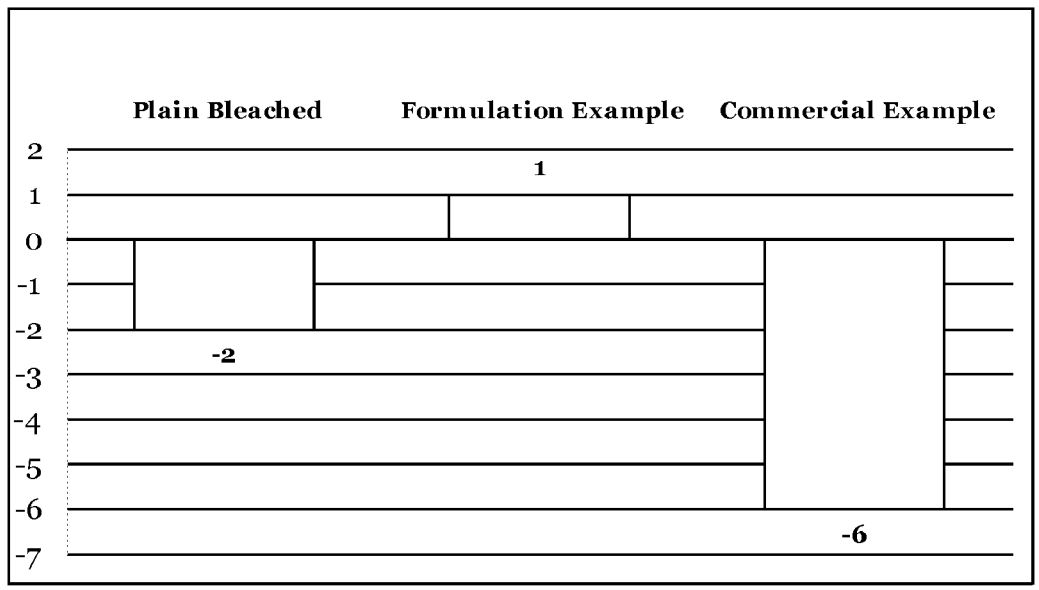
FIG. 4 depicts the results of the comparison of FIG. 3, with the parameters totaled.
Figure 5:
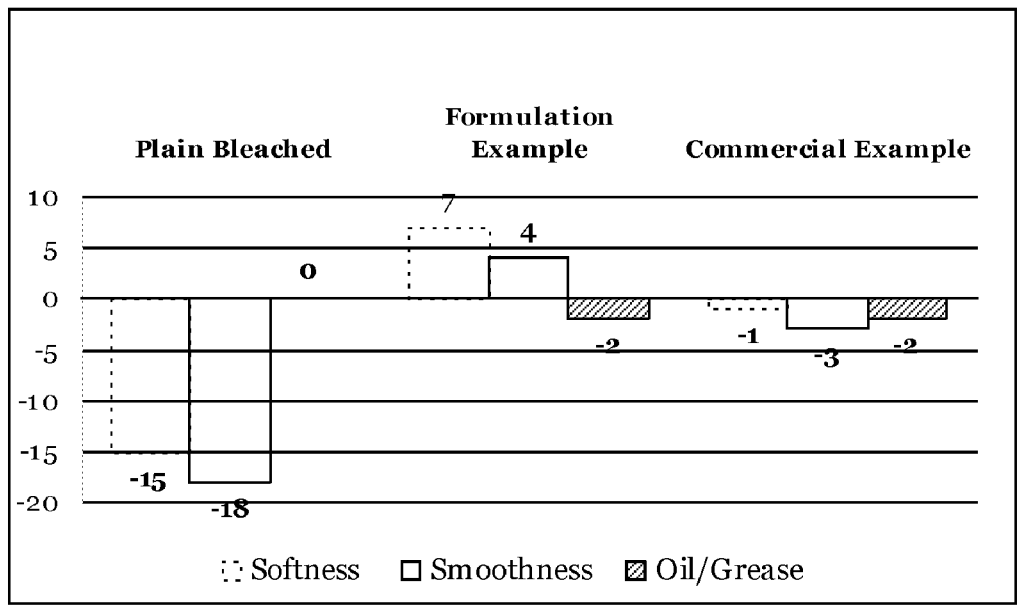
FIG. 5 depicts the results of a feel test comparison, similar to FIG. 1, except conducted on the most severely damaged hair.
Figure 6:
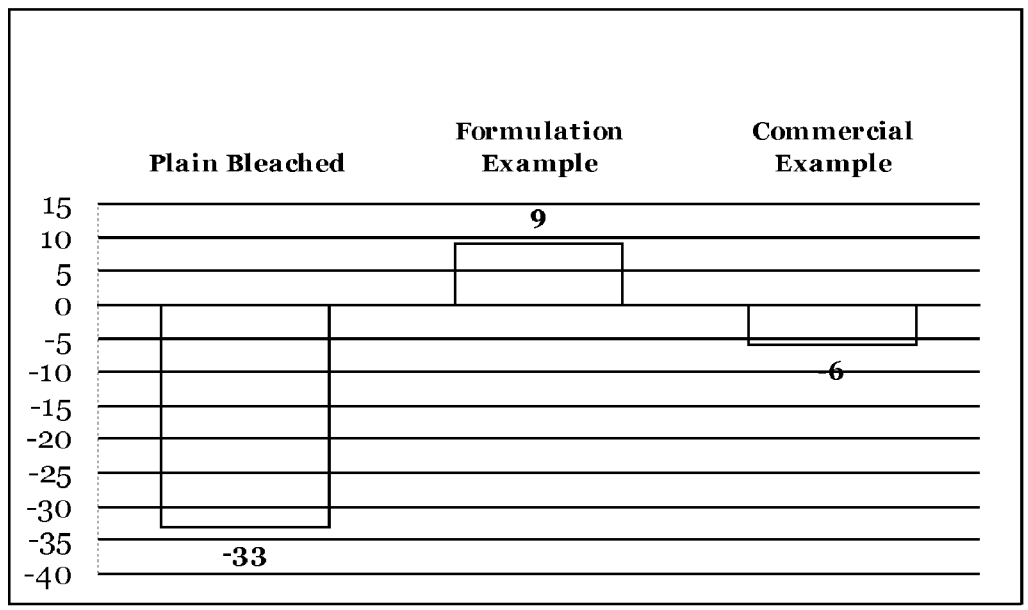
FIG. 6 depicts the results of the comparison of FIG. 5, with the parameters totaled.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., and specific functional groups are generally defined as described therein. Additionally, general principles of organic chemistry, as well as specific functional moieties and reactivity, are described in *Organic Chemistry*, Thomas Sorrell, University Science Books, Sausalito (1999), the entire contents of which are incorporated herein by reference.

Unless expressly stated otherwise, the compounds and groups described herein may be substituted with any number of substituents or functional moieties permitted by the valences of the respective compound or group. In general, the term "substituted" whether preceded by the term "optionally" or not, and substituents contained in formulas of this invention, refer to the replacement of hydrogen atoms in a given structure with a specified substituent. Unless stated otherwise, when more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen, oxygen or sulfur, may be bonded to hydrogen atoms or be substituted with any permissible substituents of organic compounds described herein which satisfy the valencies of the heteroatoms.

Where a carbon atom in a chain may be replaced with a heteroatom, this is also sometimes referred to as a "substitution."

The term acyl as used herein refers to a group having the general formula —C(O)R, where R is alkyl, alkenyl, alkynyl, aryl, carbocylic, heterocyclic, or aromatic heterocyclic. An example of an acyl group is acetyl. The term acyloxy refers to the group —OC(O)R, which forms an ester when bonded to another chemical group.

The term aliphatic, as used herein, refers to a saturated or unsaturated, straight chain (i.e., unbranched), branched, acyclic, cyclic, or polycyclic hydrocarbon backbone, which is optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties.

The term alkyl as used herein refers to a saturated, straight- or branched-chain hydrocarbon group derived from a hydrocarbon containing between one and thirty carbon atoms by removal of a single hydrogen atom. In some embodiments, the alkyl group contains 1-10 carbon atoms. In another embodiment, the alkyl group contains 1-8 carbon atoms. In still other embodiments, the alkyl group contains 1-6 carbon atoms. In yet another embodiment, the alkyl group contains 1-4 carbons. Examples of alkyl groups include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. As used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl," and the like, encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The term alkoxy as used herein refers to a saturated (i.e., alkyl-O—) or unsaturated (i.e., alkenyl-O— and alkynyl-O—) group attached to the parent molecular moiety through an oxygen atom. In certain embodiments, the alkyl, alkenyl or alkynyl group contains 1-20 aliphatic carbon atoms. In certain other embodiments, the alkyl, alkenyl, and alkynyl groups employed in the alkoxy groups of the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples include, but are not limited to, methoxy, ethoxy, propoxy, isopropoxy, n-butoxy, tert-butoxy, i-butoxy, sec-butoxy, neopentoxy, n-hexoxy, and the like.

The term alkenyl denotes a monovalent group derived from a hydrocarbon moiety having at least one carbon-carbon double bond by the removal of a single hydrogen atom. In certain embodiments, the alkenyl group employed in the invention contains 1-20 carbon atoms. In some embodiments, the alkenyl group employed in the invention contains 1-10 carbon atoms. In another embodiment, the alkenyl group employed contains 1-8 carbon atoms. In still other embodiments, the alkenyl group contains 1-6 carbon atoms. In yet another embodiment, the alkenyl group contains 1-4 carbons. Alkenyl groups include, for example, ethenyl, propenyl, butenyl, 1-methyl-2-buten-1-yl, and the like.

The term alkynyl as used herein refers to a monovalent group derived from a hydrocarbon having at least one carbon-carbon triple bond by the removal of a single hydrogen atom. In certain embodiments, the alkynyl group employed in the invention contains 1-20 carbon atoms. In some embodiments, the alkynyl group employed in the invention contains 1-10 carbon atoms. In another embodiment, the alkynyl group employed contains 1-8 carbon atoms. In still other embodiments, the alkynyl group contains 1-6 carbon atoms. Representative alkynyl groups include, but are not limited to, ethynyl, 2-propynyl (propargyl), 1-propynyl, and the like.

The term alkylamino refers to a group having the structure —NHR' wherein R' is an alkyl group, as previously defined (examples include methylamino and ethylamino); and the term dialkylamino refers to a group having the structure —NR'R", wherein R' and R" are each independently selected from the group consisting of alkyl groups (examples include dimethylamino, diethylamino and methylethylamino). The term trialkylamino refers to a group having the structure —NR'R"R''', wherein R', R", and R''' are each independently selected from the group consisting of alkyl groups. In certain embodiments, the alkyl group contain 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contain 1-6 aliphatic carbon atoms. In yet other embodiments, the alkyl group contain 1-4 aliphatic carbon atoms. Additionally, R', R", and/or R''' taken together may optionally be —$(CH_2)_k$— where k is an integer from 2 to 6, to form a ring (piperidino is an example).

An amino group, as used herein, encompasses alkylamino, dialkylamino and trialkylamino groups (as defined above), and aminoalkyl likewise includes —$RNH_2$, —RNHR', —RNR'R" and —RNR'R"R'''. A tertiary amine as used herein is an organic compound in which all three hydrogens of ammonia are replaced with organic groups. A tertiary amine may include a diamine, in which two amino groups are linked.

The term aromatic, as used herein, refers to a moiety having delocalized electrons due to conjugated double bonds, which may form a ring (as in an aryl moiety); heteroaromatic means an aromatic compound in which at least one of the atoms in the ring or aromatic chain is a nitrogen, oxygen, phosphorus, silicon or sulfur atom.

In general, the terms aryl and heteroaryl, as used herein, refer to mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, aryl refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term heteroaryl, as used herein, refers to a cyclic aromatic group having from five to ten ring atoms of which one ring atom is selected from S, O, and N; zero, one, or two ring atoms are additional heteroatoms independently selected from S, O, and N; and the remaining ring atoms are carbon, the group being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

A carboxyl group, as used herein, refers to the radical —$CO_2H$. A carboxyl group is sometimes referred to herein as a hydroxycarbonyl group. The term carboxylic acid as used herein refers to a compound with a terminal —CO$_2$H group.

The terms halo and halogen as used herein refer to an atom selected from fluorine, chlorine, bromine, and iodine.

The term heteroaliphatic, as used herein, refers to an aliphatic moiety in which one or more carbon atoms in the backbone is replaced with an oxygen, sulfur, nitrogen, phosphorus, or silicon atom, i.e., in place of carbon atoms in the chain. Heteroaliphatic moieties may be branched, unbranched, cyclic or acyclic and include saturated and unsaturated heterocycles such as morpholino, pyrrolidinyl, etc.

The term heterocyclic, as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term aromatic heterocyclic, as used herein, refers to a cyclic aromatic group having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the group being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide.

The term carbonyldioxyl, as used herein, refers to a carbonate group of the formula —O—CO—OR.

The term carbamoyl, as used herein, refers to an amide group of the formula —CONH$_2$.

The term thiohydroxyl or thiol, as used herein, refers to a group of the formula —SH.

The term ureido, as used herein, refers to a group of the formula —NH—CO—NH$_2$

The following are more general terms used throughout the present application:

As used herein, the singular forms "a", "an", and "the" include the plural reference unless the context clearly indicates otherwise. Thus, for example, a reference to "a monomer" includes a plurality of such monomers.

The term "keratin" as used herein refers any one of a class of fibrous structural proteins found in hair, wool, and nails. Keratin proteins contains a large quantity of cysteine residues.

The term organic group refers broadly to any carbon-containing group.

The term perfluorinated as used herein means a chemical group in which all the hydrogen atoms are replaced with fluorine atoms.

The term polymer refers to a molecule having three or more repeating monomer units. A repeating unit is a unit bonded directly to a plurality of like units to form a linear chain. Preferred compounds herein are non-polymeric. However, in embodiments, portions of the compound used in a composition according to the invention may contain a polymeric polyethylene or polyethylene glycol chain or other polymeric moiety.

A surface property of hair as used herein is broadly construed to refer to any change in the surface of the hair caused by applying a composition according to the invention. This may refer to the surface energy (which may be measured on a surface other than the hair itself, using contact angle measurements, for example, or other methodology); frictional attributes of the hair; resistance to moisture (measured by vapor sorption/desorption (DVS) tests, for example, or other methodology), resistance to dirt (measured by a starch test, for example). In preferred embodiments, a surface property pertains to hair conditioning, so that the property of interest is the smoothness, softness, ease of detangling, shine, or amelioration of frizz. Although these attributes may be somewhat subjective, methodologies for testing them (including the "feel test" described herein) are widely used in the art.

Synthesis

The compounds useful in the compositions and methods of the invention may be prepared by reacting a tertiary amine with a fluorinated epoxide according to the following general schemes:

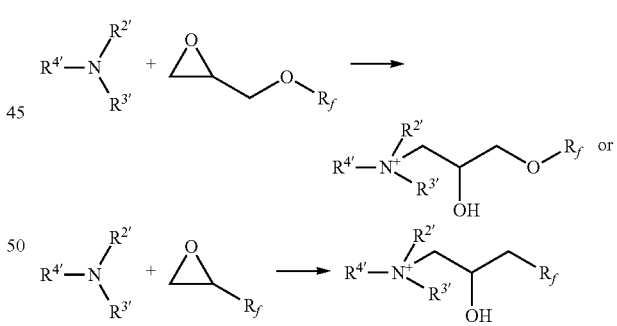

R$^{2'}$, R$^{3'}$ and R$^{4'}$ in the above reaction schemes may be the same or different organic groups, which may be substituted or unsubstituted. For example, R$^{2'}$, R$^{3'}$ and R$^{4'}$ may be C$_{1-6}$ alkyl groups, which may be substituted with hydroxyl, carboxy, alkoxy or acyloxy groups.

In the above reaction scheme, any tertiary amine may be used. In embodiments R$^{2'}$, R$^{3'}$ and R$^{4'}$ are the same or different aliphatic, heteroaliphatic, alkoxy, aryl or heteroaryl, any of which may be substituted or unsubstituted. In preferred embodiments, R$^{2'}$, R$^{3'}$ and R$^{4'}$ are C$_{1-30}$ alkyl groups, which may be substituted with hydroxyl or hydroxycarbonyl groups. Diamines and cyclic amines may also be used. In embodiments R$^{2'}$, R$^{3'}$ and R$^{4'}$ may be also independently substituted with one or more fluorine atoms. $R_f$ is a fluorinated organic group, such as $C_{1-30}$ branched or straight chain fluorinated alkyl, which may be perfluorinated or non-perfluorinated; for example, $R_f$ may comprise a $CH_2CHF$ or $CF_2$ group adjacent the epoxide moiety in the reactant and adjacent the hydroxyl carbon in the reaction product.

In embodiments, the tertiary amine is a diamine, which may be reacted with a fluorinated epoxide according to the following reaction schemes. Consistent with the reactions above, in which a tertiary amine is used, a fluorinated epoxide without an ether linkage could also be used (not shown).

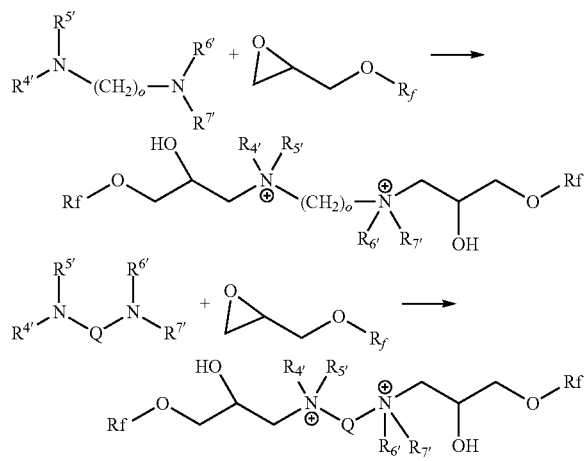

In the above reaction scheme $R^{4'}$, $R^{5'}$, $R^{6'}$ and $R^{7'}$ are the same or different organic groups, which may be substituted or unsubstituted. In embodiments, $R^{4'}$, $R^{5'}$, $R^{6'}$ and $R^{7'}$ are $C_{1-6}$ alkyl groups, which may be substituted with hydroxyl, carboxy, alkoxy or acyloxy. $R_f$ is a fluorinated organic group, such as $C_{1-30}$ branched or straight chain fluorinated alkyl, which may be perfluorinated or non-perfluorinated. The amine moieties of the diamine in the scheme above may be linked by a $C_{1-20}$ alkenyl group, so that o in the first reaction scheme above is 1 to 20. Alternatively, another linking group may be used, such as a divalent alkyl, alkenyl, alkynyl, alkoxy, cycloalkyl, aryl, acyl, acyloxy, heterocycloalkyl, hydroxyalkyl, thioalkyl; aliphatic; heteroaliphatic; cycloaryl; or heteroaryl group; any of which may be substituted or unsubstituted, linear or branched. For example, Q may be $-(CH_2)_t-$; $-(CH_2CH_2O)t-$; $-(CH_2CH(CH_3)-O)t-$; $-(CH_2CH(OH)-CH_2)t-$; $-(CH_2C(=O))t-$; $-(CH_2S-CH2)t-$ (wherein t is an integer from 1 to 10,000).

In the above reaction schemes, any reactive fluoro epoxy compound may be used, provided that it contains at least two fluorine atoms. Thus, $R_f$ may be, without limitation, a branched or straight chain fluorinated aliphatic group, a straight or branched chain fluorinated heteroaliphatic group, a fluorinated acyl group, a fluorinated aryl or fluorinated heteroaryl group. $R_f$ may be $R^1$-A-, wherein A is $CH_2$, CFH, or $CF_2$, preferably $CH_2$, and $R^1$ is an organic group containing at least two fluorine atoms. $R_f$ may include $-(CF_2)_m-$, wherein m is an integer from 1 to 20.

If a hydroxy-reactive terminated linker is used in the synthesis of Rf, such as functionalized PEG, PPG, or other polyglycol, Rf may include a linking moiety having a formula such as $-(CH_2-CH_2-O)_p-$, wherein p is an integers from 1 to 10000, depending on the molecular weight of the starting material.

Thus, in embodiments, the invention is a hair treatment composition comprising the reaction product of a fluorinated epoxide and a tertiary amine according to the reaction schemes described above. In preferred embodiments, the reaction product is the reaction product of a fluorinated epoxide and a tertiary amine selected from the group consisting of: trimethylamine; triethylamine; triisopropylamine; tributylamine methyldiethylamine; triethanolamine; triisopropanolamine; N-ethyldiethanolamine; N,N-dimethylethanolamine; N,N-diethylethanolamine; 3-diethylaminopropanol; 1,3-bis(dimethylamino)-2-propanol; 5-diethylamino-2-pentanol; 1-diethylamino-2-propanol; 2-(diethylamino)-1,2-propandiol; 2-(diisopropylamino)ethanol; 3-diisopropylamino-1,2-propandiol; 1-dimethylamino-2-propanol; 3-dimethylamino-1-propanol; 3-dimethylaminopropylamine; tris(3-aminopropyl)amine; N,N,N',N'-tetramethylethylenediamine and triethylenediamine; 1-(2-dimethylaminoethyl)-4-methylpiperazine; 2,2',2'',2'''-ethylenedinitrilotetraethanol; N,N,N',N'-tetrakis(2-hydroxypropyl)ethylenediamine; and N,N,N',N'',N''-pentamethyldiethylenetriamine.

The fluorinatedepoxides, glycidyl 2,2,3,3,4,4,5,5-octafluoropentyl ether and glycidyl 2,2,3,3,4,4,5,5,6,6,7,7,8,8,9,9 hexadecafluorononyl ether, used in the examples herein, are commercially available from Sigma-Aldrich, Inc. (St. Louis, Mo.). 2-(4,4,5,5-tetrafluoro-2-oxapentypoxirane) and 3-(1,1,2,2-Tetrafluoroethoxy)-1,2-propenoxide were obtained from Synquest Labs (Alachua, Fla.). Other fluorinated epoxides that can also be used include, 3-(1H,1H,9H-Perfluorononyloxy)-1,2-propenoxide.

Perfluorinated species which can be used in the invention include 1,2-epoxyperfluoroethane, 1,2-epoxyperfluoropropane, 1,2-epoxyperfluoroisobutane, 1,2-epoxyperfluorobutane, 2,3-epoxyperfluorobutane, 2,3-epoxyperfluoro-2-methylbutane, 2,3-epoxy-perfluoro-2,3-dimethylbutane, 1,2-epoxyperfluoropentane, 2,3-epoxyperfluoropentane, 1,2-epoxyperfluoro-2-ethylbutane, 1,2-epoxyperfluorooctane, 1,2-epoxyperfluoro-1-cyclohexylethane, 1,2-epoxyperfluoro-1,2-dicyclohexylethane, 1,2-epoxyperfluoro-2-cyclohexyl-2-methyl-propane, perfluoroepoxyethylbenzene, perfluoro-(p-epoxyethyl)-toluene, 1,2-epoxyperfluoro-1,2-diphenylethane, 1H,1H-Heptafluorobutyl epoxide, 4,5,5,6,6,6-Hexafluoro-2-(trifluoromethypbutyl epoxide, nonafluorobutylepoxide, (2,2,2-Trifluoroethyl)oxirane, 2-(Trifluoromethyl)oxirane, 2,2-Bis(trifluoromethyl)oxirane, 3-(Nonafluoro-tert-butyl)propen-1,2-oxide, 2-(2,2,3,3,3-Pentafluoropropoxymethyl)oxirane, 3-(1H,1H,9H-Perfluorononyloxy)-1,2-propenoxide, 2-(1H,1H-Nonafluoropentyl)oxirane, 2-(1H,1H-Perfluoroundecyl) oxirane, 2-(1H,1H-Perfluoroheptyl)oxirane, 3-(Perfluoro-3-methylbutyl)-1,2-propenoxide, 3-(Perfluoro-5-methylhexyl)-1,2-propenoxide, 3-(Perfluoro-7-methyloctyl)-1,2-propenoxide, 3-(Perfluorooctyl)-1,2-epoxypropane, 1,4-Bis(epoxypropyl)octafluorobutane, and so forth. The synthesis of some of these compounds is described in U.S. Pat. No. 3,622,601. The non-perfluorinated analogs of these compounds may also be used.

In embodiments, Rf in the reaction scheme above is a $C_{2-30}$ fluoroalkyl group. In preferred embodiments, Rf is not perfluorinated. For example, Rf is a straight chain $C_{2-30}$ fluoroalkyl group with a terminal $CHF_2$ group, as in many of the examples below.

Non-limiting examples of amine starting materials used according to the invention include: trimethylamine, triethylamine, triisopropylamine, tributylamine and methyldiethylamine. Those having active hydrogens include triethanolamine, triisopropanolamine, N-ethyldiethanolamine, N,N- dimethylethanolamine, N,N-diethylethanolamine, 3-diethylaminopropanol, 1,3-bis(dimethylamino)-2-propanol, 5-diethylamino-2-pentanol, 1-diethylamino-2-propanol, 2-(diethylamino)-1,2-propandiol, 2-(diisopropylamino)ethanol, 3-diisopropylamino-1,2-propandiol, 1-dimethylamino-2-propanol, 3-dimethylamino-1-propanol, 3-dimethylaminopropylamine and tris(3-aminopropyl)amine.

Depending on the structure of the amine starting material, a variety of physiochemical properties such as solubility, melting temperature, viscosity, charge density may be targeted and obtained. One such example is to alter the optical properties of the cationic fluorinated alcohol by selecting high or low refractive amines resulting in high shine or high color contrast respectively. However, in some cases the following tertiary amines may be used: bis(2-hydroxyethyl)cocoamine, polyoxyethylene cocoamine, bis(2-hydroxy ethyl) soyamine, polyoxyethylene soyamine, bis(2-hydroxyethyl) tallow amine, polyoxyethylene tallowamine, bis(2-hydroxyethyl)oleylamine, polyoxyethylene oleylamine, bis (2-hydroxyethyl)octadecylamine, polyoxyethylene octadecylamine, N,N-dimethyl-dodecylamine, N,N-dimethyl-tetradecylamine, N,N-dimethyl-hexadecylamine, N,N dimethyl-octadecylamine, N,N-dimethyl-cocoamine, N,N-dimethyl soya amine, N,N-dimethyl-tallowamine, N,N-dimethyl-oleylamine, and N-methyl-distearylamine.

Examples herein were variously prepared using triethylamine and triethanolamine, obtained from Sigma-Aldrich (St. Louis, Mo.); N,N,N',N'-tetramethylethylenediamine and triethylenediamine; 1-(2-dimethylaminoethyl)-4-methylpiperazine, 2,2',2'',2'''-ethylenedinitrilotetraethanol; N,N,N',N'-tetrakis(2-hydroxypropyl)ethylenediamine; and N,N,N',N'',N'''-pentamethyldiethylenetriamine, purchased from TCI America (Portland, Oreg.); and N,N'-dimethylpiperazine and hexamethylenetetramine, purchased from Acros Chemicals.

Additional information about the reaction to form cationic alcohols according to the invention may be found in Zeno W. Wicks, et al., *Organic Coatings: Science and Technology*, John Wiley (1999), p 278, incorporated by reference.

SYNTHETIC EXAMPLE 1

A cationic fluorinated alcohol according to the invention, (Example 1 in Table 1 below) was made according to the following reaction scheme:

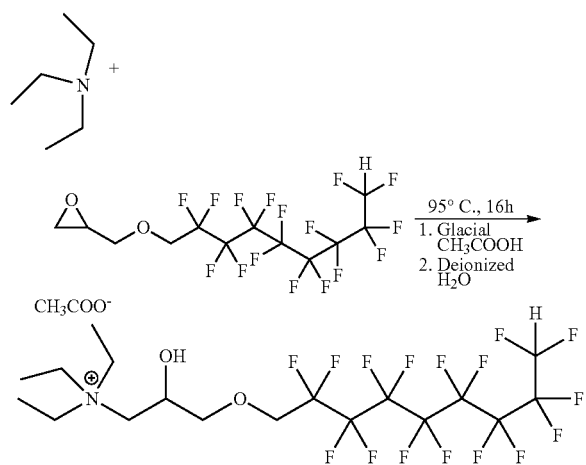

To 1 equivalent (0.308 g, 3.042 mmol) of triethylamine in a 7 ml scintillation vial with stirbar, 1 equivalent (0.174 ml) of glacial acetic acid was added and mixed well. 0.28 ml of de-ionized water was added so that the amine was dissolved or well dispersed. 1.01 equivalents (1.5 g, 3.073 mmol) of Glycidyl 2,2,3,3,4,4,5,5,6,6,7,7,8,8,9,9-hexadecafluorononyl ether were added and the mixture was uniformly stirred at high speed at 95° C. The fluorinated epoxide separated into a different layer. After about 4 to 6 hours, the two layers became homogeneous indicating that the reaction was near completion. The mixture was stirred continuously overnight (about 16 hours). At the end of the reaction, a uniform clear solution was obtained. The water was removed under vacuum and the viscous product was re-dissolved 2-3 times in absolute ethanol to remove any remaining water. The mixture was purified by repeated precipitation (about 3-5 times) from diethyl ether with hexane. Once the last wash, hexane was added to the material to form a slurry. The excess hexane wasdecanted off and the gel-like material is dried under vacuum overnight, to yield a beige wax. $^1$H NMR was performed on a Varian Mercury 300 MHz spectrometer. Mass Spectrometry was conducted using a Thermo Finnigan LCQ-deca mass spectrometer. $^1$H NMR δ (CD$_3$OD, 300 MHz): 1.31 (t, 3H, —CH$_2$CH$_3$), 1.92 (t, 3H, CH$_3$COO$^-$), 3.49 (m, 8H, N$^+$(CH$_2$)4), 3.71 (t, 2H, —OCH$_2$CF$_2$—), 4.18 (m, 2H,— CH(OH)CH$_2$O—), 4.27 (m, 1H, —CH(OH)CH$_2$O—), 6.70 (t, 1H, —CF$_2$CHF$_2$). (+)-ESIMS 590.18 [M$^+$].

In an alternative synthesis, hydrochloric acid was used instead of glacial acetic acid: 5.0 ml of water was added to 1.05 equivalent (1.48 g, 10.754 mmol) of triethylamine hydrochloride in a 20 ml scintillation vial with stirbar to dissolve the salt completely and was mixed well. A clear solution was obtained. 1.0 equivalent (5.0 g, 10.242 mmol) of Glycidyl 2,2,3,3,4,4,5,5,6,6,7,7,8,8,9,9-hexadecafluorononyl ether (HDFE) was added. The HDFE separated into a different layer at the bottom of the vial. The mixture was uniformly stirred at high speed at 95° C. After about 2 hours, the 2 layers became homogeneous and clear indicating that the reaction was near completion. The solution was colorless to pale yellow. The mixture was left stirring overnight for a total of about 16 hours. Acetone was added to the solution and the water was removed under vacuum. This step was repeated 3 times to ensure that most of the water was removed. The product was warmed and dissolved in a minimal volume of diethyl ether. Cold hexane was added dropwise and the vial was cooled in an ice bath. The solid precipitated from the solution. The solvents were removed by decantation. This precipitation step was repeated 3 times until a clear gel-like material was obtained. The product was dried under vacuum to yield a white wax.

The cationic compounds disclosed herein may be associated with any counter ion to form cosmetically acceptable salts, and the depiction of the cationic compound is intended to include all such salts. The synthesis examples above, for example, demonstrate the formation of acetate and chloride salts, but others are known to those of ordinary skill in the art. A reference Lists of suitable cosmetically acceptable salts are found in *Remington's Pharmaceutical Sciences*, 17th ed., Mack Publishing Company, Easton, Pa., 1985, p. 1418.

SYNTHETIC EXAMPLE 2

A cationic fluorinated alcohol according to Example 2 in Table 1 below was synthesized as follows: to 1 equivalent (0.392 g, 3.433 mmol) of N,N'-Dimethylpiperazine in a 7 ml scintillation vial with stirbar, 1 equivalent (0.393 ml) of glacial acetic acid was added and mixed well. 0.4 ml of de-ionized water was added so that the amine was well dispersed. 2.02 equivalents (2.0 g, 6.941 mmol) of glycidyl 2,2,3,3,4,4,5,5-octafluoropentyl ether was added and the mixture was uniformly stirred at high speed at 95° C. After about 4 to 6 hours, the two layers become homogeneous indicating that the reaction was near completion. The mixture was stirred continuously overnight (about 16 hours). At the end of the reaction, a uniform clear solution was obtained. The water was removed under vacuum and the viscous product was re-dissolved 2-3 times in absolute ethanol to remove any remaining water. The mixture was purified by repeated precipitation (about 3-5 times) from diethyl ether with hexane. The excess hexane was decanted off and the viscous material was dried under vacuum overnight. A pale yellow liquid was obtained. NMR confirmed the identify of the molecule as the second entry in Table 1 below.

SYNTHETIC EXAMPLE 3

The cationic alcohol of Example 15 in Table 1 was prepared according to the following reaction scheme:

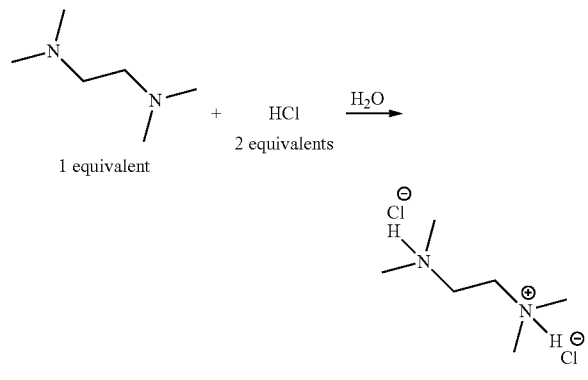

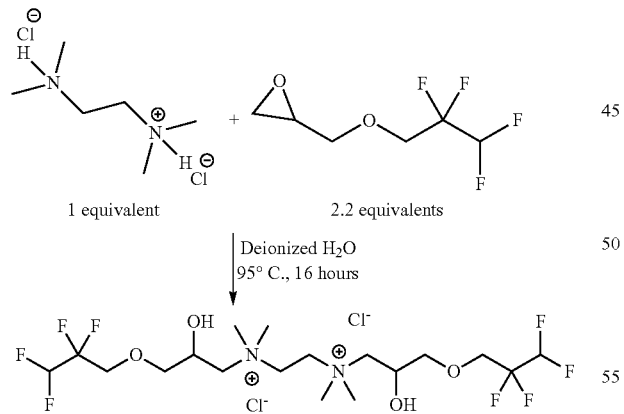

An intermediate salt N,N,N',N'-Tetramethylethylenediamine Di-Hydrochloride ("TEMED-HCl") was prepared as shown in step 1 by weighing 1 equivalent (20 g, 172.06 mmol) of N,N,N',N'-Tetramethylethylenediamine (TEMED; Aldrich, 99.5% purity) into a 500 ml round bottom flask containing a magnetic stir bar. 20 g of de-ionized water was added and the mixture was stirred at room temperature until a uniform clear solution was obtained. 2.09 equivalents (36 g, 360 mmol) of 10N HCl was weighed into a graduated dropping funnel with a pressure equalizing arm. The round bottom flask was set up in an ice-bath and the dropping funnel was attached. The HCl was slowly added over about one hour with constant stirring in the ice-bath. After complete addition, the reaction mixture was allowed to react further for one hour. The resulting clear solution was concentrated under reduced pressure using a rotovap followed by repeated co-evaporations with acetone to yield a white crystalline solid. The solid was washed a few times with hexane and cold diethyl ether to remove any impurities and dried under vacuum to yield 31 g (95%) of a white crystalline solid. $^1$H NMR (300 MHz, D$_2$O, 25° C.): δ 2.90 (t, 12H); 3.65 (d, 4H).

To 1 equivalent (41.6 g, 222.3 mmol) of TEMED-HCl salt prepared in step 1, 100 ml of water was added and mixed until a clear solution was obtained. 2.2 equivalents (92.0 g, 489 mmol) of glycidyl 2,2,3,3-tetrafluoropropyl ether was added dropwise using a dropping funnel over a period of 2 hours. The mixture was uniformly stirred at high speed at 95° C. and left stirring for a total of 16 h until a clear homogeneous solution was obtained. The solution was then washed with dichloromethane three times and the aqueous solution was evaporated to dryness under vacuum. The oily residue was then stripped from acetone and evaporated to dryness. The final obtained waxy residue was dried in a vacuum oven at a temperature of 50° C. overnight to give a white powder. The purity of the crystalline final product was analyzed by HPLC and gave a result of 98.1%. The final obtained yield was 75.3 g (60%) of a white crystalline solid. $^1$H NMR (300 MHz, D$_2$O, 25° C.): δ 3.35 (dd, 12H); 3.60 (m, 4H), 3.72 (d, 4H); 4.10) (m, 8H); 4.45 (m, 2H); 6.25 (tt, 2H).

SYNTHETIC EXAMPLE 4

The cationic alcohol of Example 4 in Table 1 was prepared according to the following reaction scheme:

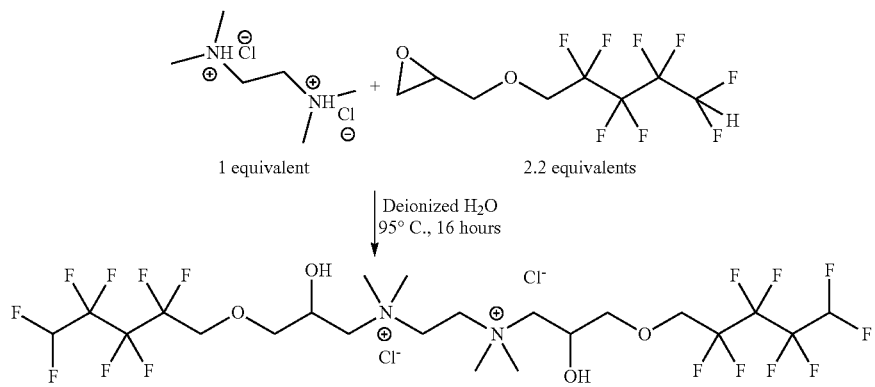

In the above synthetic scheme, 3.5 ml of de-ionized water was added to 1.0 equivalent (1.49 g, 7.88 mmol) of TEMED-HCl in a 20 ml scintillation vial with stirbar and mixed well until a clear solution was obtained. 2.2 equivalents (5.0 g, 17.35 mmol) of glycidyl 2,2,3,3,4,4,5,5-octafluoropentyl ether were added. The fluoro epoxide separated into a different layer at the bottom of the vial. The mixture was uniformly stirred at high speed at 95° C. The cloudy mixture was left stirring overnight. At the end of 16 hours, a homogeneous, clear solution was obtained. The aqueous solution was washed with dichloromethane to remove impurities. The aqueous layer was then concentrated under reduced pressure using a rotovap. The material was re-dissolved 2 to 3 times in absolute acetone and concentrated again using a rotovap to remove any remaining water. A sticky material was obtained. The mixture was purified by repeated precipitation (3 to 5 times) from acetone with hexane. The solution was decanted off and the precipitate dried under vacuum overnight yielding approximately 3.7 g (80%) of a white/beige powder. $^1$H NMR (300 MHz, D$_2$O, 25° C.): δ 3.30 (dd, 12H); 3.58 (m, 4H), 3.75 (d, 4H); 4.03 (m, 2H); 4.19 (t, 6H); 4.50 (m, 2H); 6.49 (tt, 2H).

TABLE 1

| Example No. | Chemical Structure |
|---|---|
| Example 1 | 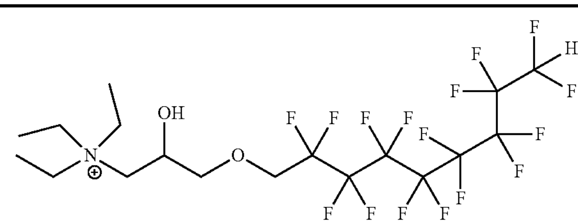 |
| Example 2 | 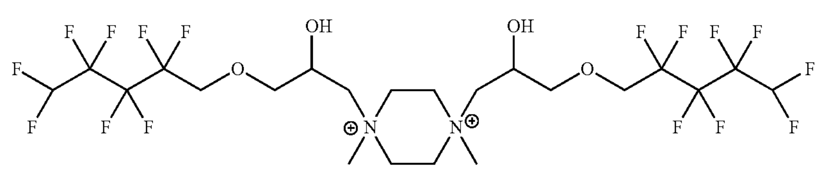 |
| Example 3 | 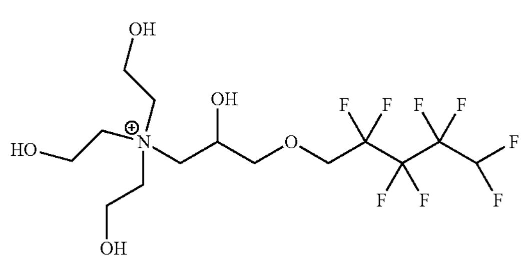 |
| Example 4 | 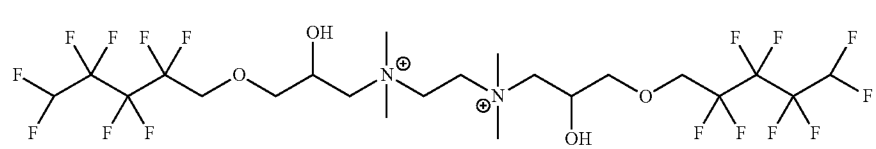 |

TABLE 1-continued
| Example No. | Chemical Structure |
|---|---|
| Example 5 | 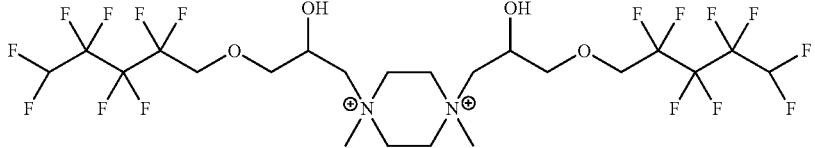 |
| Example 6 | 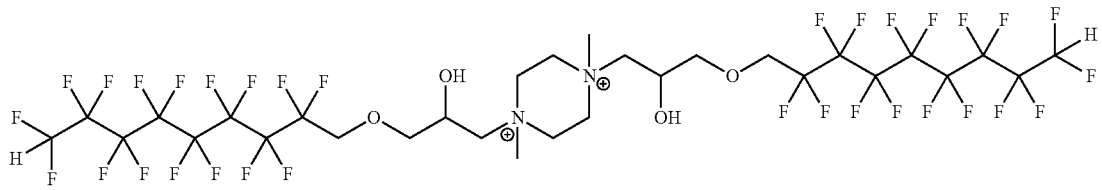 |
| Example 7 | 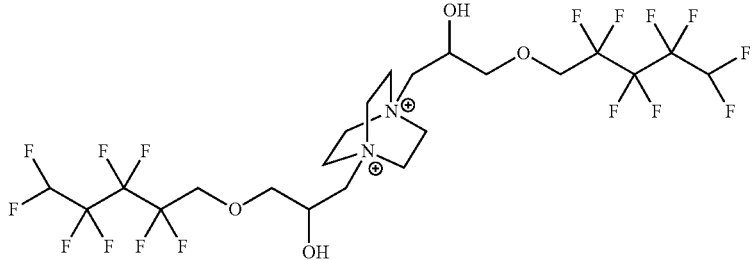 |
| Example 8 | 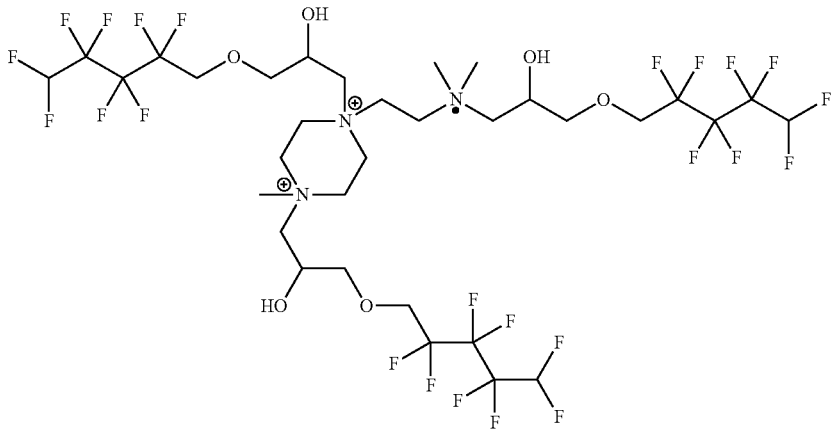 |
| Example 9 | 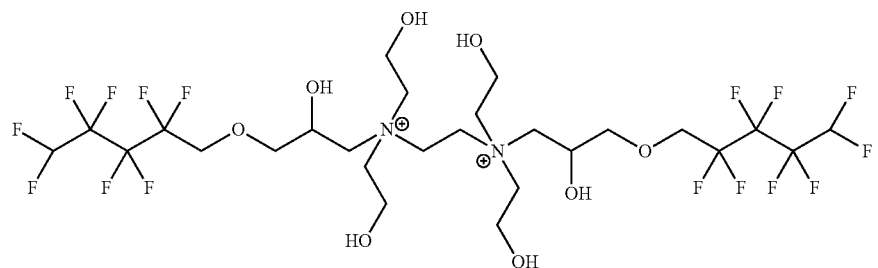 |
| Example 10 | 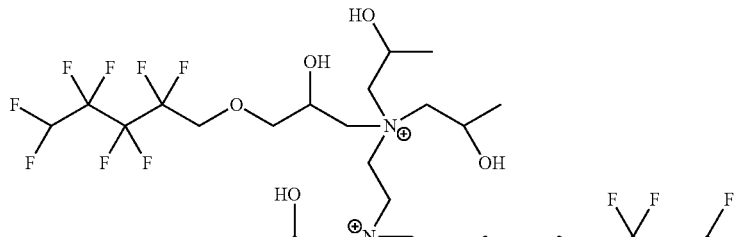 |

Formulations

The compositions of the invention may be formulated with any cosmetically acceptable excipient and may be in the form of a spray, cream, lotion, emulsion, gel, wax, or pomade, for example. Conditioners, shampoos, sprays and creams are presently preferred formulations.

The cationic fluorinated alcohol according to the invention may be present in an amount up to about 99 percent by weight, in embodiments up to 75 percent by weight, in other embodiments up to 50 percent by weight, and preferably in a range of about 0.1 to about 10.0 percent by weight. Cosmetically acceptable excipients include those described below, preferably provided in the general amounts set forth in the formulation examples below. However, departure from these guidelines is to be expected and is best left to the skill of the formulator.

The compositions may include other cosmetically active ingredients, to provide cleansing, conditioning, setting, relaxing, volumizing or other cosmetically desired effects. Thus, a composition according to the invention may be formulated as a shampoo, conditioner, mask, leave-in conditioner, and/or styling product such as a spray, cream, mousse, or gel and may be provided in combination with a dye, bleach or formulation intended to straighten or wave hair, for example, in which case another cosmetically active ingredient would be provided in the composition in addition to the fluorinated compound described herein, to provide the desired effect. Additional charged ingredients (cationic, anionic, or zwitterionic) may be used to affect deposition properties.

Cosmetically acceptable excipients used in the hair care industry can be broken down into several catergories. Components from a category may be included or excluded from the final hair care composition depending on the use of the final composition (e.g., hair spray, conditioner, shampoo). The categories of excipients include: (1) preservatives/antioxidants/chelating agents; (2) sunscreen agents; (3) vitamins; (4) dyes/hair coloring agents; (4) proteins/amino acids; (5) plant extracts; (6) humectants; (7) fragrances/perfumes; (8) oils/emollients/lubricants/butters; (9) penetrants; (10) thickeners/viscosity modifiers; (11) polymers/resins/hair fixatives/film formers; (12) surfactants/detergents/emulsifiers/opacifying agents; (13) volatiles/propellants/solvents; (14) liquid vehicles/solvents; (15) salts; (16) pH adjusting agents/buffers/neutralizing agents; (17) hair conditioning agents; (18) anti-static agents/anti-frizz agents; (19) antidandruff agents; (20) hair waving/straightening agents; and (21) absorbents. Many suitable excipients falling into these categories may be identified from standard reference texts in the cosmetics industry, and only a few illustrative examples are provided herein. Moreover, some excipients may fall into more than one category.

Preservatives/Antioxidants/Chelating Agents

The inventive cosmetic hair care compositions may include preservatives, antioxidants, and/or chelating agents to extend the shelf-life and/or prevent the degradation of the components of the inventive composition. Exemplary preservative, antioxidants, and chelating agents useful in the inventive hair care compositions include, without limitation, ethylenediamine tetraacetic acid (EDTA) and salts thereof (e.g., disodium EDTA), citric acid and salts thereof, methylisothiazolinone, and BHT. In embodiments, a cosmetic composition according to the invention may include 0% to approximately 5% by weight of such ingredients.

Sunscreen Agents

The inventive cosmetic hair care compositions may include a sunscreen agent to protect the treated hair from the damaging ultraviolet rays of the sun. In certain embodiments, the sunscreen agent protects the treated hair from damaging UV-A and/or UV-B rays. Exemplary sunscreen agents useful in the inventive hair care compositions include, without limitation, p-aminobenzoic acid (PABA), and PABA-derivatives (e.g., allantoin PABA, butyl PABA) which may be provided in an amount of approximately 0.0001% to approximately 5% by weight of the cosmetic composition, for example.

Vitamins

The inventive cosmetic hair care compositions may include one or more vitamins to nourish or replenish the treated hair. In embodiments, the cosmetic composition includes approximately 0.001% to approximately 5% by weight of one or more vitamins.

Dyes/Hair Coloring Agents

The inventive cosmetic hair care compositions may include a dye or other hair coloring agent (e.g., a stain), including permanent, semi-permanent and temporary dyes. Such materials are well known in the art and may be provided in an amount of 0.0001% to 5% by weight of the cosmetic composition.

Proteins/Amino Acids

The inventive cosmetic hair care compositions may include a protein, peptide, or amino acid. Such components may be added to the inventive composition to nourish the hair, impart a desired characteristic to hair (e.g., increase shine, increase body), or impart a desired characteristic to the composition (e.g., thickening the composition). Exemplary proteins that may be added to hair care compositions include, without limitation, silkprotein, soy protein, and wheat protein. As would be appreciated by one of ordinary skill in the art, derivatives, mutants, fusion proteins, fragments, or combinations of any of these proteins may also be included in the inventive cosmetic hair care composition. In certain embodiments, the proteins, peptides, or amino acids may be included in the composition in a range from about 0.0001% to about 10% by weight.

Plant Extracts

The inventive cosmetic hair care compositions may include an extract from a plant. Plant extract may be added to the inventive composition to nourish the hair, provide a fragrance or color to the composition, impart a desired characteristic on hair, or impart a desired characteristic to the composition. Extracts may be prepared from any part of a plant, including leaves, fruit, flower, grass, vegetable, nut, root, stem, bark, and the like, according to methods known in the art. A plant extract is typically used in an amount ranging from 0.001 to 10.0% by weight of the total composition.

Humectants

The inventive cosmetic hair care compositions may include a humectant. A humectant is a hydrogroscopic substance. It is typically a chemical compound containing hydrophilipic groups such as hydroxyl groups, amines, carboxylates, etc. Humectants are typically found in hair care compositions to reduce static and/or to provide a moisturizing quality to the hair care composition. The humectants attract and holds moisture on the hair. Non-limiting examples of humectants useful in the inventive hair care compositions include glycerin, glycerol, hyaluronic acid, propylene glycol. In certain embodiments, the humectant is used in the hair care composition in an amount ranging from about 1% to about 10% by weight of the composition.

Fragrances/Perfumes

The inventive cosmetic hair care compositions may optionally include a fragrance or perfume. The perfume or fragrance may be used in the hair care composition in an amount ranging from 0.0001% to 10% by weight, typically in an amount ranging from 0.01% to 1% by weight.

Oils/Emollients/Lubricants/Butters

The inventive cosmetic hair care compositions may include an oil, emollient, lubricant, or butter. Oils are used in hair care compositions to moisturize and/or nourish the hair. Generally, an oil is any fatty substance which is liquid at room temperature (25° C.). Examplary oils, emollients, lubricants, and butters include PPG-3 benzyl ether myristate, linear and/or branched fatty alcohols and fatty acid esters, glyceryl stearate, PEG and castor oils.

Penetrants

The inventive cosmetic hair care compositions may include a penetrant to enhance the penetration of the formulation into hair. The concentration of the penetrant in the composition may range from 1% to 50% by weight of the composition. In certain embodiments, the concentration of penetrant ranges from 1% to 25% by weight.

Thickeners/Viscosity Modifiers

The inventive cosmetic hair care compositions may include a thickening agent or a viscosity modifier. The thickening agent may be a natural or synthetic thickening agent. In certain embodiments, the thickening agent is polymeric. In certain embodiments, the thickening agent is a polysaccharide. In certain embodiments, the thickening agent is a protein. In certain embodiments, the thickening agent is a low melting point wax. Non-limiting examples of low melting point waxes include fatty alcohols, such as stearyl alcohol, cetearyl alcohol, behenyl alcohol, and the like. Non-limiting examples of synthetic polymeric thickeners include polymers of acrylic acid, methacrylic acid and their simple esters, which may be co-polymerized with one or more organic groups such as ethoxylated or propoxylated polymeric moieties. Non-limiting examples of such synthetic polymeric thickeners include acrylamides copolymer PEG-150 pentaerythrityl tetrastearate, PEG-6 caprylic/capric glycerides, polyacrylate-1 crosspolymer, and xanthan gum. In embodiments, the concentration of thickening agent is in a range of 2% to 50% by weight.

Polymers/Resins/Hair Fixatives/Film Formers

Polymers, resins, hair fixatives, or film-forming agents may be used in certain of the the inventive cosmetic hair care compositions at a concentration to achieve the desired result when applied to hair. In embodiments polyquaternium compounds, such as Polyquaternium-16, may be used as film formers. In certain embodiments, the polymer, resin, hair fixative, or film-forming agent is used in the final composition in a range from about 0.01% to about 20% by weight.

Surfactants/Detergents/Emulsifiers/Opacifiers

Surfactants, detergents, emulsifiers, and the like may be used in the inventive cosmetic hair care compositions. Such agents may work to make the final composition homogenous or help to solubilize certain ingredients of the composition. Exemplary surfactants useful in the present invention include sodium lauroyl methyl isethionate, sodium methyl cocoyl taurate, sodium dodecyl sulfate, cocoamidopropyl betaine, and sodium laureth sulfate, sodium lauryl sulfate, alkyl and alkyl ether sulfates. Suitable emulsifiers include, without limitation, cetyl alcohol and cetearyl alcohol. Many surfactants and emulsifiers useful in the inventive compositionss are described in McCutcheon's Detergents And Emulsifiers, 1984 Annual, published by Allured Publishing Corporation, which is incorporated herein by reference. An exemplary opacifier is glycol stearate. In embodiments, the inventive compositions may contain a such ingredients in the range of from about 0.01% to about 20% by weight.

Propellants

Various inventive hair care compositions (such as hair sprays, particularly aerosols) contain a propellant used to expell the inventive composition from a pressurized container. Both liquids and gases can be used as propellants. Exemplary propellants useful in the hair care compositions according to the invention include, without limitation, butane, dimethyl ether, and hydrofluorocarbon 152a.

Solvent

The inventive hair care compositions typically include a solvent or combination of solvents to dissolve or solubilize the components of the composition. The solvent typically makes up the balance of a composition. Exemplary organic solvents useful in the inventive hair care compositions include, without limitation denatured ethyl alcohol, isopropyl alcohol and butylene glycol. In certain embodiments, water is used as the solvent, alone or in combination with one or more organic solvents. One or more solvents may make up from 1% to 99% by weight of the composition.

Salts

Various salts may also be added to the inventive hair care compositions. Salts are typically ionized and result in stoichiometrically equivalent amounts of cations and anions when dissolved in a solution. Salts are typically soluble in water. The salt used in the inventive compositions may be an inorganic salt or an organic salt. Salts are typically used in hair care compositions as thickening agents, buffering agents, hair waving agents, humectants, and/or oxidizing or reducing agents. Typically the concentration of the salt in the final composition is in a range from about 1% to about 30% by weight.

pH Adjusting Agents/Buffers/Neutralizing Agents

The inventive hair care compositions may include pH adjusting agents, buffers, neutralizing agents, and the like. Such agents may be used to lower the pH, raise the pH, or maintain the pH of the final composition at a particular level. The concentration of the pH adjusting agent, buffer, or neutralizing agent in the final composition is generally in the range from about 0.01% to about 10% by weight.

Hair Conditioning Agents

Hair conditioning agents may also be optionally included in the inventive cosmetic hair care compositions. Such agents may be included in shampoos, conditioners, styling products, or hair sprays. Exemplary conditioners include pantothenyl ethyl ether, behentrimonium chloride, behentrimonium methosulfate, cocamidopropyl betaine, hydrolyzed hair keratin, hydrolyzed wheat protein, and hydroxypropyl guar hydroxypropyltrimonium chloride, to name a few. The concentration of the hair conditioning agent in the final composition is typically in the range from about 0.01% to about 10% by weight.

Anti-Static Agents/Anti-Frizz Agents

Anti-static agents and/or anti-frizz agents may also be optionally included in the inventive cosmetic hair care compositions. Such agents are particularly useful in hair conditioners, styling products, or hair sprays. An example of an antistatic agent is linoleamidopropyl PG-dimonium chloride phosphate. Typically, anti-static or anti-frizz agent, when used, is present in a range of about 0.01% to about 5% by weight.

Antidandruff Agents

Antidandruff agents may also be included in inventive hair care compositions. In the U.S., antidandruff agents are defined in 21 C.F.R. §358.703(b), (c), and (d) and are listed in 21 C.F.R. §358.710. The concentration of the antidandruff agent in the cosmetic composition may be in the range from about 0.001% to about 10% by weight.

Hair Waving Agents/Hair Straightening Agents

The inventive hair compositions may also optionally include hair waving agents or hair straightening agents. Such agents are used to modify hair fibers to facilitate permanent configurational changes. In certain embodiments, the agents are reducing agents which work to disrupt disulfide linkages in hair. In certain embodiments, strong alkaline agents are used as hair straightening agents. The concentration of the hair waving/hair straightening agent in the final hair care composition may be in a range from about 0.001% to about 20% by weight.

Absorbents

Certain hair care compositions of the present invention include absorbents. In certain embodiments, the inventive hair care composition with an absorbent is a dry shampoo. Absorbents are typically ingredients with a large surface area which can attract other materials such as lipids. The concentration of the absorbent in the final composition may range from about 1% to about 50% by weight of the cosmetic composition.

The methods of treating hair according to the invention require only that the hair be contacted with the composition, and the methods may be the same as, or combined with, conventional methods for hair treatment. For example, and not by way of limitation, the method may include a step of shampooing the hair followed by rinsing, a step of conditioning the hair followed by rinsing, a step of spraying the hair to provide set or other cosmetic advantage, not immediately followed by rinsing, or a step of working a lotion into the hair, not immediately followed by rinsing. In embodiments, a method according to the invention involves a treatment of the hair after a bleaching or dying operation. Other possibilities for providing improved feel and hydrophobicity to hair, in different hair care contexts, would be apparent to one of ordinary skill in the art.

The compositions are often aqueous. Water, or a mixture of water and a lower alcohol, may be present in an amount of about 50 percent by weight to about 99 percent by weight.

Non-limiting examples of compositions ranges for different formulations of the cationic fluorinated alcohol include the following:

FORMULATION EXAMPLE 1

An exemplary styling spray according to the invention contains

| Ingredients | % w/w |
| --- | --- |
| Water | q.s. |
| Cationic Fluorinated Alcohol | 0.1-10.00 |
| Preservative | 0.05-1.25 |

FORMULATION EXAMPLE 2

An exemplary simple shampoo according to the invention contains

| Ingredients | % w/w |
| --- | --- |
| Water | q.s. |
| Cationic Fluorinated Alcohol | 0.1-10.00 |
| Sodium Lauroyl Methyl Isethionate | 5.00-17.00 |
| Sodium Methyl Cocoyl Taurate | 5.00-17.00 |
| Cocamidopropyl Betaine | 5.00-17.00 |
| Ethylenediaminetetraacetic acid | 0.1-0.4 |
| PEG-150 Pentaerythrityl Tetrastearate | 0.1-2.00 |
| PEG-6 Caprylic/Capric Glycerides | 0.1-2.00 |
| Preservative | 0.05-1.25 |

FORMULATION EXAMPLE 3

An exemplary simple conditioner according to the invention includes

| Ingredients | % w/w |
| --- | --- |
| Water | q.s. |
| Cationic Fluorinated Alcohol | 0.1-10.00 |
| Cetearyl Alcohol | 4.00-8.00 |
| Behentrimonium Chloride | 0.50-3.00 |
| Preservative | 0.05-1.25 |

FORMULATION EXAMPLE 4

An exemplary leave-in conditioner according to the invention includes

| Ingredients | % w/w |
| --- | --- |
| Water | |
| Polyacrylate-1 Crosspolymer | 0-1% |
| Emulsifying Wax NF | 0-8% |
| Glycol Stearate | 0-5% |
| Behentrimonium Methosulfate | 0.5-5% |
| Cetyl Alcohol | 0.2-5% |
| Butylene Glycol | 0-1% |
| PPG-3 Benzyl Ether Myristate | 0-5% |
| Panthenol | 0-2% |
| Glycerin | 0-10% |
| Fragrance | 0.1-1% |
| Phenoxyethanol | 0.3-0.5% |
| Methylisothiazolinone | 0.05-0.1% |
| Lauryl Methyl Gluceth-10 Hydroxypropyldimonium Chloride | 0-5% |
| Cationic Fluorinated Alcohol | 0.1-5% |

FORMULATION EXAMPLE 5

Another exemplary hair treatment spray according to the invention includes

| Ingredients | % w/w |
| --- | --- |
| Water | |
| Behentrimonium Methosulfate | 0.5-1% |
| Cetyl Alcohol | 0.2-0.5% |
| Butylene Glycol | 0-0.5% |
| PPG-3 Benzyl Ether Myristate | 0-1% |
| Lauryl Methyl Gluceth-10 Hydroxypropyldimonium Chloride | 0-0.5% |
| Pantothenyl Ethyl Ether | 0-1% |

-continued

| Ingredients | % w/w |
|---|---|
| Linoleamidopropyl PG-dimonium Chloride Phosphate | 0-0.5% |
| Polyquaternium-16 | 0-0.5% |
| Fragrance | 0-1% |
| Phenoxyethanol | 0.3-0.5% |
| Methylisothiazolinone | 0.05-0.1% |
| Cationic Fluorinated Alcohol | 0.1-5% |

Performance Criteria

Hair treated with the composition performs well in standard "feel tests" when tested against certain prior art compositions. Repeated applications with the compositions according to the invention yield increased deposition of the active compound on hair.

Feel Test

In order to test the performance of a shampoo and conditioner prepared according to the invention against a prior art formulation, shampoo and conditioner compositions were prepared based on Formulation Examples 2 and 3 above, using 2 wt % the compound of Example 2 above. This was tested against a leading commercial "damage repair" shampoo and conditioner: Plain bleached hair was used as an internal control.

To prepare the samples for the feel test, 6 g of virgin medium brown hair was bleached using: 30 g of ultra concentrated bleach powder (Clairol) well mixed with 70 ml of 40V Hydrogen peroxide solution (Pure White, Clairol). The paste was manually worked into the hair fibers to saturate the samples. The samples were sandwiched in aluminum sheets and placed in an oven at 50° C. for 30 minutes for "level 1" damage. A 7.5% solution of sodium lauryl sulfate solution was used to shampoo the tresses and they were blow-dried for a few minutes and allowed to air-dry at room temperature for at least 2 hours. For "level 2" damage, the tress was bleached a second time following the same procedure, but for only 20 minutes and at room temperature. For "level 3" damage, the level 1 damaged tress is bleached using the same amounts as before, but for 20 minutes at 50° C. in an oven.

The protocol for shampooing and conditioning was as follows: The hair was wetted for 10 seconds. 350 mg of shampoo was applied to 1.5 g of hair. The hair was lathered for 30 seconds and rinsed for another 30 seconds. The tress was blotted between paper towels and 350 mg of the conditioner was applied to the hair. The conditioner was worked through the hair for 30 seconds, followed by rinsing for another 30 seconds. The tress was then blotted dry and blow-dried straight if necessary.

For each feel test, the respective virgin hair is used as the control. The first tress is evaluated with respect to the control and assessed in attributes such as softness, smoothness, and oil residue/grease. Each attribute is rated with respect to the control as shown in Table 2. Between the evaluation of each tress, hands are washed and dried.

TABLE 2

| Positive Rating for Attribute | | Negative Rating for Attribute | |
|---|---|---|---|
| 0 | Feels like virgin hair | −1 | Slightly worse than the control |
| +1 | Slightly better, Barely noticeable | −2 | Noticeably not as good as the control |
| +2 | Noticeably better | −3 | Undesirable |
| +3 | Exceptionally better | | |

TABLE 2-continued

| Positive Rating for Attribute | Negative Rating for Attribute |
|---|---|

Figure 7:
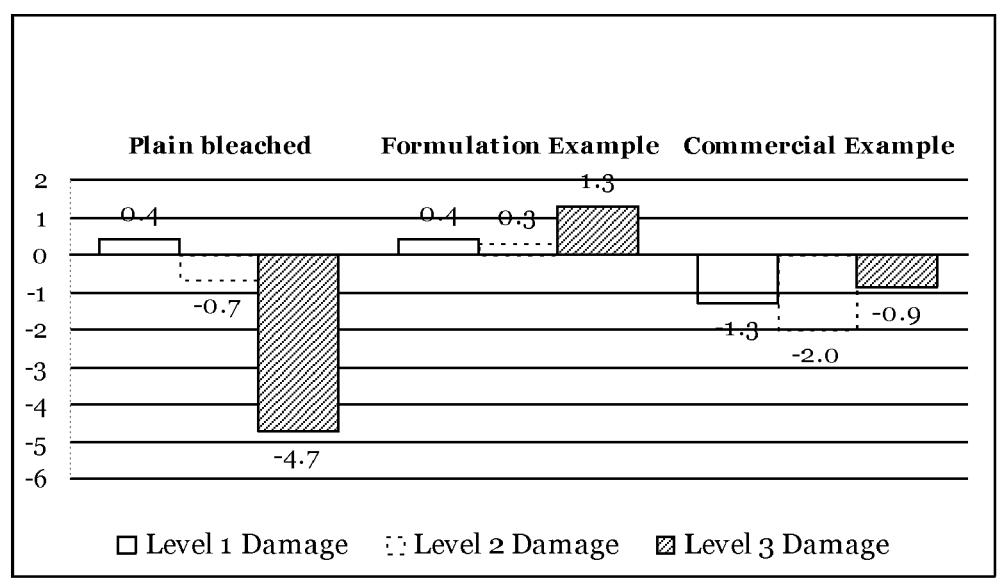
FIG. 7 graphically shows an improvement in feel test comparison scores for a composition according to the invention for increasing levels of damage.

As shown in FIG. 1 through FIG. 6, the scores for each attribute at each level of damage were plotted, as were the scores for combined attributes. The compositions according to the invention showed a better feel performance at every level of damage compared to the prior art. As shown in FIG. 7, the compositions according to the invention show an improvement in feel scores as the level of damage increases.

Contact Angle Measurements

As described previously, improving upon benefits such as hydrophobicity, shine and tactile properties leads to the perception of healthier, more conditioned hair. Contact angle measurement has proven to be a viable method to measure the degree of hydrophobicity of hair. In principle, it measures the angle at the point of contact of a liquid with a surface. If the surface is highly hydrophobic (such as virgin, untreated hair), the angle of the water droplet at the interface would be greater than 90°. Likewise, a hydrophilic surface would cause the water droplet to fall flat, and the angle would be close to 0°.

Virgin black hair tresses (1.5 g each, from International Hair Importers) were bleached once with a homogeneous mixture of Clairol Pure White 20V hydrogen peroxide solution (45 ml) and Clairol bleach powder Ultra Concentrate BW2000 (6.75 g) for 10 min at 50° C. The tresses were shampooed with a 7.5% Sodium Lauryl Sulfate solution twice and air-dried for 24 h. A separate tress was kept aside and used without any further treatment in the contact angle experiment and referred to as: Plain Bleached. Additionally, an untreated virgin black tress was used as hydrophobic control. The hair was shampooed twice with 7.5% Sodium Lauryl Sulfate solution, air-dried for 24 h and labeled as: Virgin.

To one of the bleached tresses, 0.2 g of shampoo S1 from Table 3 was applied and lathered for 20 s, followed by a 20 s rinse under running water. The wet tress was blotted in paper towels until the water had stopped dripping and 0.2 g of conditioner C1 from Table 4 was then applied to the hair. It was continuously spread through the fibers for 20 s and was followed by a 20 s rinse. These 2 steps were denoted as one shampoo-conditioner cycle. The cycle was repeated for another 19 times to a total of 20 cycles. The tress was then labeled as: 20× Placebo.

An additional bleached tress was shampooed and conditioned 20 times following the procedure as described above using shampoo S1 and conditioner C2 (from Table 5). The tress was labeled as: 20× Active.

Contact angle measurements were performed with a Calm DCA-312 tensiometer. The tensiometer motor and balance were calibrated prior to use. ASTM Type II distilled water (BDH-1168, lot 092409A) was used as the liquid. The water surface tension was determined with a platinum DuNuoy ring (Cat 14-812-5) to be 70.6 mN/m. The water was changed out between each sample.

The hair fiber diameter was measured with a precision micrometer (Mitutoyo Cat 293-761-30). Individual hair fibers were mounted in the tensiometer grip and immersed at the top speed range of 20-264 micrometers/sec. The advancing and receding contact angles were measured for each sample, with runs performed in triplicate. The results are shown in Table 6.

TABLE 3

Shampoo formula S1

| Ingredients | (w/w) % |
| --- | --- |
| Water | Q.S. |
| Polyquaternium-47 | 0.75 |
| Ethylenediaminetetraacetic acid | 0.3 |
| Sodium Lauroyl Methyl Isethionate | 10.25 |
| Sodium Methyl Cocoyl Taurate | 13.3 |
| Cocamidopropyl Betaine | 14.21 |
| Behenyl Alcohol | 0.2 |
| Laureth-4 | 0.15 |
| Laureth-23 | 0.45 |
| Lactamide MEA | 3.0 |
| PEG-7 Glyceryl Cocoate | 3.0 |
| Fragrance | 0.8 |
| Hydrolyzed wheat protein | 1.0 |
| Methylisothiazolinone/Methylchloroisothiazolinone | 0.04 |
| PEG-150 Pentaerythrityl Tetrastearate (and) PEG-6 Caprylic/Capric Glycerides | 1.2 |

TABLE 4

Conditioner formula C1

| Ingredients | (w/w) % |
| --- | --- |
| Water | Q.S. |
| Guar Hydroxypropyltrimonium Chloride | 0.25 |
| Citric Acid, (1% solution) | 0.57 |
| Quaternium 87 | 2.0 |
| Cetearyl Alcohol | 6.0 |
| Behentrimonium Chloride | 2.0 |
| Hydrolyzed wheat protein | 1.0 |
| Methylisothiazolinone/Methylchloroisothiazolinone | 0.04 |
| Fragrance | 1.0 |

TABLE 5

Conditioner formula C2

| Ingredients | (w/w) % |
| --- | --- |
| Water | Q.S. |
| Guar Hydroxypropyltrimonium Chloride | 0.25 |
| Citric Acid, (1% solution) | 0.57 |
| Quaternium 87 | 2.0 |
| Cetearyl Alcohol | 6.0 |
| Behentrimonium Chloride | 2.0 |
| Hydrolyzed wheat protein | 1.0 |
| Methylisothiazolinone/Methylchloroisothiazolinone | 0.04 |
| Fragrance | 1.0 |
| Cationic Fluorinated Alcohol (Example 15 from Table 1) | 1.5 |

TABLE 6

Contact Angle measurements of hair fiber after various treatments

| Sample Identification | Average Advancing Angle (°) | Standard Deviation (°) |
| --- | --- | --- |
| Virgin | 86.8 | 1.5 |
| Plain Bleached | 36.3 | 8.4 |
| 20x Placebo | 42.9 | 8.3 |
| 20x Active | 71.1 | 2.1 |

The results from the contact angle measurements as described in Table 6 demonstrate a significant difference in hydrophobicity between bleached and virgin hair as the Virgin sample displays a contact angle twice that of the Plain Bleached sample.

As observed in Table 6, the use of the placebo conditioner containing standard cationic and conditioning compounds (20x Placebo) did not significantly impact the hydrophilic nature of the bleached hair. However, the addition of 1.5% cationic fluorinated alcohol Example 15 in from Table 1 to conditioner C2 (20x Active) significantly increased the contact angle of the bleached hair nearing that of the Virgin sample, signifying improved hydrophobicity. This data suggests that the 20x Active treated hair may behave more like virgin, undamaged hair in regards to water uptake, swelling, and friction, leading to improved fell, look and manageability of hair.

The foregoing description of the preferred embodiments is exemplary only and not to be considered as limiting the invention, which is defined by the appended claims.

What is claimed is:

1. A compound according to the following formula:

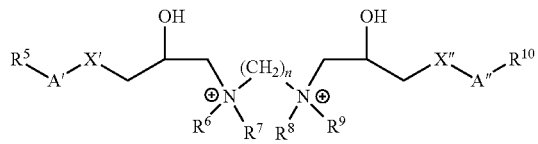

wherein,

A' and A" are independently $CH_2$, CHF or $CF_2$;

X' and X" are independently O, $CF_2$, or —$(CH_2)_m$—;

$R^5$ and $R^{10}$ are the same or different organic groups, each substituted with at least two fluorine atoms;

$R^6$ and $R^9$ are independently substituted or unsubstituted $C_{1-6}$ alkyl, and $R^6$ and $R^9$ may join to form a ring;

$R^7$ and $R^8$ are independently substituted or unsubstituted $C_{1-6}$ alkyl, and $R^7$ and $R^8$ may join to form a ring;

n is an integer from 1 to 6; and m is an integer from 1 to 20, including cosmetically acceptable salts thereof.

2. A compound according to claim 1, wherein A' and A" are $CH_2$.

3. A compound according to claim 1, wherein X' and X" are $CH_2$.

4. A compound according to claim 1, wherein X' and X" are O.

5. A compound according to claim 1, wherein $R^5$ and $R^{10}$ are the same straight or branched chain $C_{1-30}$ fluoroalkyl group.

6. A compound according to claim 5, wherein $R^5$ and $R^{10}$ each have a terminal $CHF_2$ group.

7. A compound according to claim 1, wherein $R^6$, $R^7$, $R^8$, and $R^9$ are independently $C_{1-6}$ alkyl groups, optionally substituted with a hydroxyl group, carboxyl group, alkoxy group or acyloxy group, and wherein $R^6$ and $R^8$ are the same and $R^7$ and $R^9$ are the same.

8. A compound according to claim 1, wherein X' and X" are O, A' and A" are $CH_2$, $R^5$ and $R^{10}$ are the same straight or branched chain $C_{1-30}$ fluoroalkyl group having a terminal $CHF_2$ group, and wherein $R^6$ and $R^8$ are the same and $R^7$ and $R^9$ are the same.

9. A compound according to claim 8, selected from the group consisting of:

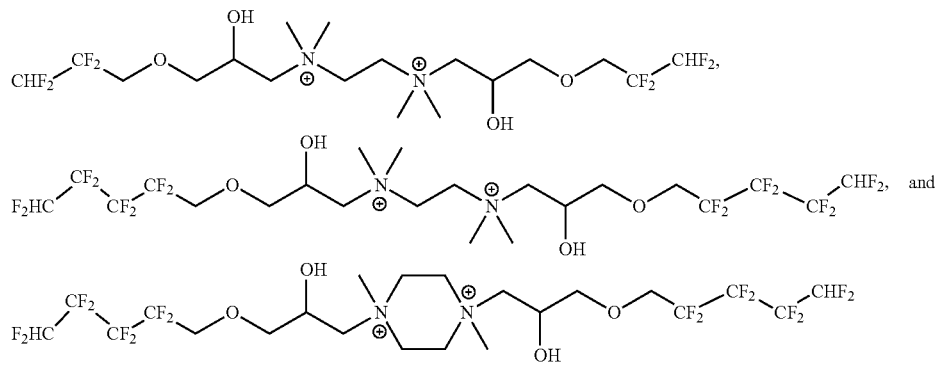

including cosmetically acceptable salts thereof.

10. A compound according to claim 1, wherein one or more of $R^6$, $R^7$, $R^8$, and $R^9$ is defined by the following formula

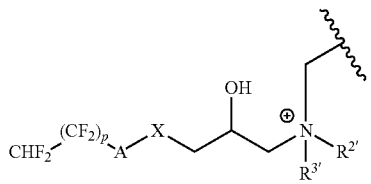

wherein,
X is O, $CF_2$, or $—(CH_2)_q—$;
A is $CH_2$, CFH or $CF_2$;
$R^{2'}$ and $R^{3'}$ are independently $C_{1-6}$ alkyl groups, optionally substituted with a hydroxyl group, carboxyl group, alkoxy group or acyloxy group, or any of $R^{2'}$, and $R^{3'}$ may join to form a ring with a quaternary nitrogen;
p is an integer from 1 to 20; and
q is an integer from 1 to 20.

11. A cosmetic composition for treating hair or skin, comprising a cosmetically acceptable excipient, and a compound of the following formula:

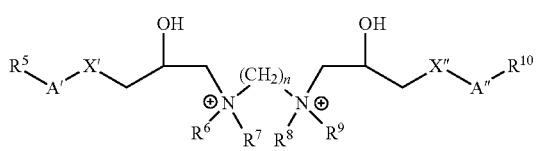

wherein,
A' and A" are independently $CH_2$, CHF or $CF_2$;
X' and X" are independently O, $CF_2$, or $—(CH_2)_m—$;
$R^5$ and $R^{10}$ are the same or different organic groups, each substituted with at least two fluorine atoms;
$R^6$ and $R^9$ are independently substituted or unsubstituted $C_{1-6}$ alkyl, and $R^6$ and $R^9$ may join to form a ring;
$R^7$ and $R^8$ are independently substituted or unsubstituted $C_{1-6}$ alkyl, and $R^7$ and $R^8$ may join to form a ring;
n is an integer from 1 to 6; and
m is an integer from 1 to 20
including cosmetically acceptable salts thereof.

12. A composition according to claim 11, wherein A' and A" are $CH_2$.

13. A composition according to claim 11, wherein X' and X" are $CH_2$.

14. A composition according to claim 11, wherein X' and X" are O.

15. A composition according to claim 11, wherein $R^5$ and $R^{10}$ are the same straight or branched chain $C_{1-30}$ fluoroalkyl group.

16. A composition according to claim 15, wherein $R^5$ and $R^{10}$ each have a terminal $CHF_2$ group.

17. A composition according to claim 11 wherein $R^6$, $R^7$, $R^8$, and $R^9$ are independently $C_{1-6}$ alkyl groups, optionally substituted with a hydroxyl group, carboxyl group, alkoxy group or acyloxy group, and wherein $R^6$ and $R^8$ are the same and $R^7$ and $R^9$ are the same.

18. A composition according to claim 11, wherein X' and X" are O, A' and A" are $CH_2$, $R^5$ and $R^{10}$ are the same straight or branched chain $C_{1-30}$ fluoroalkyl group having a terminal $CHF_2$ group, and $R^6$ and $R^8$ are the same and $R^7$ and $R^9$ are the same.

19. The composition according to claim 18, wherein the compound has the following structure:

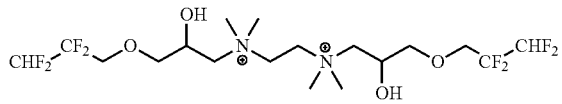

including cosmetically acceptable salts thereof.

20. A composition according to claim 11, wherein one or more of $R^6$, $R^7$, $R^8$, and $R^9$ is defined by the following formula:

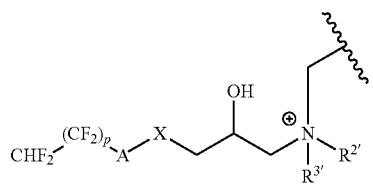

wherein,
X is O, or $—(CH_2)_q—$;
A is $CH_2$, CFH or $CF_2$;
$R^{2'}$ and $R^{3'}$ are independently hydrogen; aliphatic; heteroaliphatic; acyl; aryl; or heteroaryl; any of which may be substituted or unsubstituted; or any of $R^{2'}$, and $R^{3'}$ may join to form a ring with a quaternary nitrogen;
p is an integer from 1 to 20; and
q is an integer from 1 to 20.

21. A method of treating hair, comprising applying a composition according to claim 11 to hair.

22. A hair treatment composition comprising the reaction product of a fluorinated epoxide and a tertiary amine, including cosmetically acceptable salts of said reaction product, in a cosmetically acceptable excipient, said reaction product comprising a quaternary ammonium moiety, a hydroxyl group, and containing at least two fluorine atoms.

23. A composition according to claim 22, wherein said fluorinated epoxide and said reaction product are not perfluorinated.

24. A composition according to claim 23, wherein said fluorinated epoxide and said reaction product contain a terminal $CHF_2$ group.

25. A compound according the following formula:

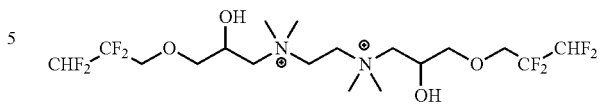

and cosmetically acceptable salts thereof.

* * * * *